United States Patent [19]

Shibata et al.

[11] 4,293,557

[45] Oct. 6, 1981

[54] ANTIULCER PHENOXYPROPYLAMINE DERIVATIVES

[75] Inventors: Kenyu Shibata, Inagi; Toshihisa Itaya; Nobuaki Yamakoshi, both of Kawasaki; Shigeru Kurata, Tokyo; Naoyuki Koizumi, Kawasaki; Masaaki Tarutani; Hideki Sakuma, both of Yokohama; Kunihiro Konishi, Kawasaki, all of Japan

[73] Assignee: Teikoku Hormone Mfg. Co., Ltd., Tokyo, Japan

[21] Appl. No.: 164,017

[22] Filed: Jun. 30, 1980

[30] Foreign Application Priority Data

Jul. 3, 1979 [JP] Japan .................................. 54-83426
Feb. 20, 1980 [JP] Japan .................................. 55-19088

[51] Int. Cl.³ .................. A61K 31/445; C07D 295/14
[52] U.S. Cl. .............................. 424/267; 260/239 B; 260/239 BF; 260/326.41; 260/326.56; 424/244; 424/274; 424/324; 546/216; 546/221; 546/232; 546/233; 546/234; 560/106; 560/251; 564/175; 564/196; 564/202; 564/213; 564/220; 564/348
[58] Field of Search ................. 546/233, 234, 221; 564/220, 196, 202, 175; 260/326.41, 239 BF; 560/106, 251; 424/267, 324, 274, 244

[56] References Cited

U.S. PATENT DOCUMENTS 3,856,812 12/1974 Dahm et al. .................. 260/326.41
3,996,279 12/1976 Schlager ......................... 546/233 X
4,128,658 12/1978 Price et al. ..................... 424/285
4,134,983 1/1979 Baldwin ......................... 546/233 X
4,156,079 5/1979 Krapcho ....................... 260/326.41 X

FOREIGN PATENT DOCUMENTS 2821410 11/1978 Fed. Rep. of Germany .
1338169 11/1973 United Kingdom .

Primary Examiner—Richard A. Schwartz
Attorney, Agent, or Firm—Wenderoth, Lind & Ponack

[57] ABSTRACT

Phenoxypropylamine derivatives of the general formula

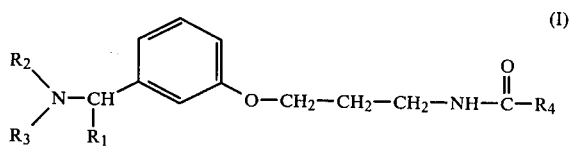

wherein $R_1$ represents a hydrogen atom or a methyl or ethyl group, $R_2$ and $R_3$, independently from each other, represent a lower alkyl group, or together form a linear alkylene group having 4 to 7 carbon atoms which may be optionally substituted by a hydroxyl or hydroxymethyl group, and $R_4$ represents a hydrogen atom or a group of the formula $—R_5—Z$ in which $R_5$ represents a lower alkylene group, and Z represents a hydrogen atom or an amino, mono- or di-(lower alkyl)-amino, hydroxy lower alkylamino, lower alkanoylamino, hydroxyl, lower alkoxy, lower alkanoyloxy, phenoxy, halophenoxy, benzoyloxy or halobenzoyloxy group, and the salts thereof; to a process for production thereof; and to their medicinal use, particularly to antiulcer agents comprising these phenoxypropylamine derivatives or their salts.

12 Claims, No Drawings

ANTIULCER PHENOXYPROPYLAMINE DERIVATIVES

This invention relates to novel phenoxypropylamine derivatives. More specifically, it relates to phenoxypropylamine derivatives of the general formula

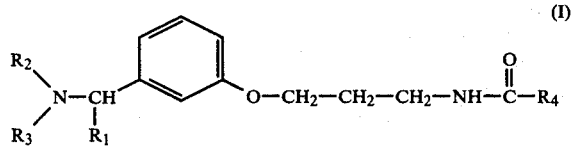

wherein $R_1$ represents a hydrogen atom or a methyl or ethyl group, $R_2$ and $R_3$, independently from each other, represent a lower alkyl group, or together form a linear alkylene group having 4 to 7 carbon atoms which may be optionally substituted by a hydroxyl or hydroxymethyl group, and $R_4$ represents a hydrogen atom or a group of the formula —$R_5$—Z in which $R_5$ represents a lower alkylene group, and Z represents a hydrogen atom or an amino, mono- or di-(lower alkyl)-amino, hydroxy lower alkylamino, lower alkanoylamino, hydroxyl, lower alkoxy, lower alkanoyloxy, phenoxy, halophenoxy, benzoyloxy or halobenzoyloxy group, and
the salts thereof; to a process for production thereof; and to their medicinal use, particularly to antiulcer agents comprising these phenoxypropylamine derivatives or their salts.

One great cause of ulcer formation in the stomach or duodenum is the excessive secretion of gastric acid, and conventional antiulcer agents for controlling hyperchlorhydria are roughly classified into those having the action of neutralizing gastric acid and those having anticholinergic activity. However, the former type is weak and short-lasting in effect, and the latter type produces strong side-effects.

It is known on the other hand that secretion of gastric acid is stimulated through a histamine $H_2$ receptor. In recent years, some novel type gastric acid secretion inhibitors having an antagonistic action against the histamine $H_2$ receptor have been developed and suggested for practical application (see, for example, British Pat. No. 1,338,169, U.S. Pat. No. 4,128,658, and West German Laid-Open Patent Publication No. 2,821,410).

The compounds of general formula (I) provided by the present invention are novel compounds not described in the prior literature. They have an excellent activity of inhibiting secretion of gastric acid based on their antagonistic action against the histamine $H_2$ receptor, and are useful as new type antiulcer agents.

In the present specification and the appended claims, the term "lower" which qualifies groups or compounds means that the group or compounds so qualified have not more than 6 carbon atoms, preferably 1 to 4 carbon atoms.

Thus, the term "lower alkyl groups" used in the present application may be linear or branched, and includes, for example, methyl, ethyl, n-propyl, isopropyl, n-butyl, isobutyl, sec-butyl, and tert-butyl. The term "mono- or di-(lower alkyl)amino group" includes, for example, methylamino, ethylamino, propylamino, isopropylamino, butylamino, dimethylamino, diethylamino, dipropylamino, and dibutylamino. The term "hydroxy lower alkylamino group" includes hydroxyethylamino, hydroxypropylamino, hydroxybutylamino, etc. The term "lower alkanoylamino group" includes, for example, acetylamino, propionylamino, and pentanoylamino. The term "lower alkoxy group" includes methoxy, ethoxy, n-propoxy, isopropoxy, etc. The term "lower alkanoyloxy group" includes, for example, acetoxy, n-propionyloxy, and isopropionyloxy.

The "halophenoxy group" and "halobenzoyloxy group" respectively mean a phenyloxy group and a phenylcarbonyloxy group having at least one, preferably 1 or 2, halogen atom on the benzene ring, and include, for example, 4-chlorophenoxy, 4-bromophenoxy, and 3,4-dichlorobenzoyloxy.

The term "halogen atom", as used in the present application, denotes chlorine, bromine, iodine and fluorine atoms, especially chlorine or bromine.

The expression "linear alkylene group having 4 to 7 carbon atoms which may be optionally substituted by a hydroxyl or hydroxymethyl group" for $R_2$ and $R_3$ taken together in formula (I) means that $R_2$ and $R_3$ are bonded together through nitrogen atom to form a 1-pyrrolidinyl, 1-piperidinyl, 1-perhydroazepinyl or 1-perhydroazocinyl group which may optionally be substituted by a hydroxyl or hydroxymethyl group.

Thus, specific examples of the moiety

in the general formula (I) are

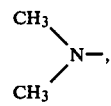

1-pyrrolidinyl group

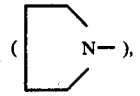

1-piperidinyl group

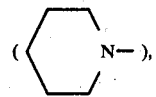

1-perhydroazepinyl group

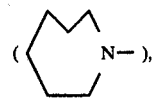

and 1-perhydroazocinyl group

and the above groups mono-substituted by a hydroxyl group (—OH) or hydroxymethyl group (—CH₂OH), such as

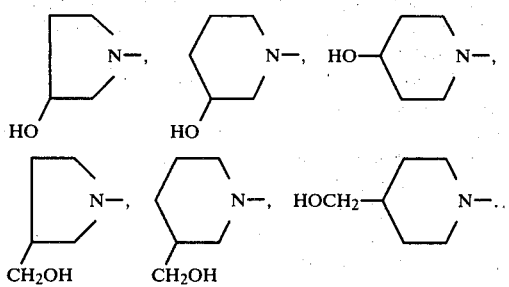

Of these, 1-pyrrolidinyl and 1-piperidinyl groups optionally substituted by a hydroxyl group are preferred. Among them

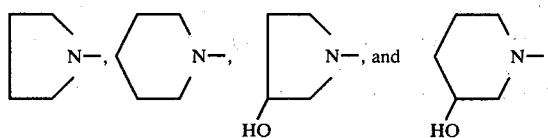

are preferred. Especially preferred are 1-pyrrolidinyl and 1-piperidinyl groups. When the above moiety represents a 1-pyrrolidinyl or 1-piperidinyl group, it is desirable from the standpoint of pharmacological effects that $R_1$ should represent a hydrogen atom or a methyl group.

In formula (I), $R_4$ represents a hydrogen atom or a group of formula —$R_5$—Z. The lower alkylene group for $R_5$ is, for example, a methylene or ethylene group, especially the methylene group. The group Z typically includes, a hydrogen atom, an amino group, an acetamino group, a methylamino group, a dimethylamino group, a hydroxyethylamino group, a hydroxypropylamino group, a hydroxyl group, a methoxy group, an ethoxy group, an acetoxy group, a propionyloxy group, a pivaloyloxy group, a phenoxy group, a 4-chlorophenoxy group, a benzoyloxy group, and 3,4-dichlorobenzoyloxy group.

In one preferred group of the compounds of general formula (I), Z may represent a hydrogen atom, or an amino, mono- or di-methylamino, hydroxyethylamino, acetylamino, hydroxyl, $C_1$-$C_2$ alkoxy, or $C_2$-$C_3$ alkanoyloxy group.

Thus, in a more preferred class of the compounds of formula (I) of this invention, $R_4$ represents a hydrogen atom or a methyl, hydroxyethylaminoethyl, hydroxymethyl, methoxymethyl, ethoxymethyl, acetoxymethyl or propionyloxymethyl group, especially a hydroxymethyl or acetoxymethyl group.

Typical examples of the compounds of formula (I) are listed below or described in Examples to be given hereinbelow.

N-[3-(3-Dimethylaminomethylphenoxy)propyl]acetoxyacetamide,
N-[3-[3-(1-diethylaminopropyl)phenoxy]propyl]acetamide,
N-[3-[3-(N'-ethyl-N'-propylaminomethyl)phenoxy]propyl]hydroxyacetamide,
N-[3-(3-dipropylaminomethylphenoxy)propyl]formamide,
N-[3-[3-[1-(pyrrolidinyl)ethyl]phenoxy]propyl]methoxyacetamide,
N-[3-[3-[1-(1-pyrrolidinyl)ethyl]phenoxy]propyl]methoxypropionamide,
N-[3-[3-[1-(1-pyrrolidinyl)ethyl]phenoxy]propyl]acetoxypropionamide,
N-[3-[3-[1-(1-pyrrolidinyl)propyl]phenoxy]propyl]hydroxyacetamide,
N-[3-[3-[1-(1-pyrrolidinyl)propyl]phenoxy]propyl]methoxyacetamide,
N-[3-[3-[1-(1-pyrrolidinyl)propyl]phenoxy]propyl]acetoxyacetamide,
N-[3-[3-(1-piperidinylmethyl)phenoxy]propyl]propionamide,
N-(2-hydroxypropionyl)-3-[3-(1-piperidinylmethyl)phenoxy]propylamine,
N-(3-hydroxypropionyl)-3-[3-(1-piperidinylmethyl)phenoxy]propylamine,
N-(5-hydroxyvaleryl)-3-[3-(1-piperidinylmethyl)phenoxy]propylamine,
N-[3-[3-(1-piperidinylmethyl)phenoxy]propyl]ethoxyacetamide,
N-[3-[3-(1-piperidinylmethyl)phenoxy]propyl]butoxyacetamide,
N-(4-methoxybutyryl)-3-[3-(1-piperidinylmethyl)phenoxy]propylamine,
N-(3-acetoxypropionyl)-3-[3-(1-piperidinylmethyl)phenoxy]propylamine,
N-(3-pivaloyloxypropionyl)-3-[3-(1-piperidinylmethyl)phenoxy]propylamine,
N-(3-propionylaminopropionyl)-3-[3-(1-piperidinylmethyl)phenoxy]propylamine,
N-(2-hydroxyethylaminoacetyl)-3-[3-(1-piperidinylmethyl)phenoxy]propylamine,
N-[5-(2-hydroxyethylamino)valeryl]-3-[3-(1-piperidinylmethyl)phenoxy]propylamine,
N-(3-diethylaminopropionyl)-3-[3-(1-piperidinylmethyl)phenoxy]propylamine,
N-(4-dimethylaminobutyryl)-3-[3-(1-piperidinylmethyl)phenoxy]propylamine,
N-[3-[3-[1-(1-piperidinyl)ethyl]phenoxy]propyl]acetoxyacetamide,
N-[3-[3-[1-(1-piperidinyl)propyl]phenoxy]propyl]acetamide,
N-[3-[3-[1-(1-piperidinyl)propyl]phenoxy]propyl]methoxyacetamide,
N-[3-[3-(1-perhydroazepinylmethyl)phenoxy]propyl]methoxyacetamide,
N-[3-[3-(1-perhydroazocinylmethyl)phenoxy]propyl]acetoxyacetamide,
N-(3-aminopropionyl)-3-[3-[1-(3-hydroxy)pyrrolidinylmethyl]phenoxy]propylamine,
N-[3-[3-[1-[1-(3-hydroxy)pyrrolidinyl]ethyl]phenoxy]propyl]acetoxyacetamide,
N-[3-[3-[1-(3-hydroxy)piperidinylmethyl]phenoxy]propyl]benzoyloxyacetamide,
N-[3-[3-[1-(3-hydroxy)piperidinylmethyl]phenoxy]propyl]butyryloxyacetamide,
N-[3-[3-[1-(4-hydroxy)piperidinylmethyl]phenoxy]propyl]methoxyacetamide,
N-[3-[3-[1-(4-hydroxymethyl)piperidinylmethyl]phenoxy]propyl]acetoxyacetamide, and
N-[3-[3-[1-(3-hydroxy)perhydroazepinylmethyl]phenoxy]propyl]formamide.

According to this invention, salts of the compounds of formula (I) are also provided. Examples of these salts are inorganic acid salts such as salts of hydrochloric acid, hydrobromic acid, sulfuric acid, nitric acid and phosphoric acid, and organic acid salts such as salts of acetic acid, propionic acid, lactic acid, citric acid, oxalic acid, tartaric acid, and p-toluenesulfonic acid. Those which are pharmaceutically acceptable are suitable.

In accordance with this invention, the compounds of formula (I) and their salts can be produced by the following various process embodiments.

(a) When obtaining a compounds of formula (I) wherein $R_4$ represents a hydrogen atom or a group of the formula $—R_5—Z$ in which $R_5$ is as defined hereinabove and Z represents the groups defined hereinabove excepting lower alkanoyloxy, benzoyloxy and halobenzoyloxy groups, a compound of the following formula

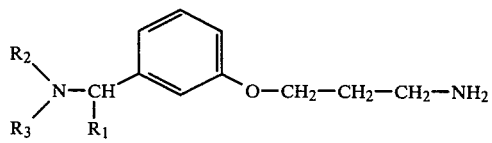 (II)

wherein $R_1$, $R_2$ and $R_3$ are as defined hereinabove, or its reactive derivative is reacted with a carboxylic acid of the following formula

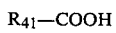 (III)

wherein $R_{41}$ represents a hydrogen atom or a group of the formula $—R_5—Z_1$ in which $R_5$ is as defined hereinabove, and $Z_1$ represents the same groups as defined for symbol Z excepting lower alkanoyloxy, benzoyloxy and halobenzoyloxy groups, or its reactive derivative.

(b) When obtaining a compound of formula (I) wherein $R_4$ represents a hydrogen atom or a group of the formula $—R_5—Z$ in which $R_5$ is as defined hereinabove and Z represents a hydrogen atom, or a mono- or di-(lower alkyl)amino, lower alkanoylamino, lower alkoxy, phenoxy or halophenoxy group, a phenol derivative of the following formula

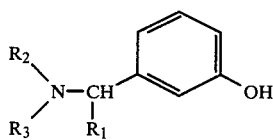 (IV)

wherein $R_1$, $R_2$ and $R_3$ are as defined hereinabove, is reacted with a propylamide derivative of the following formula

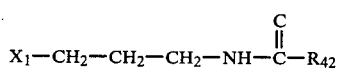 (V)

wherein $R_{42}$ represents a hydrogen atom or a group of the formula $—R_5—Z_2$ in which $R_5$ is as defined hereinabove and $Z_2$ represents a hydrogen atom, or a mono- or di-(lower alkyl)amino, lower alkanoylamino, lower alkoxy, phenoxy or halophenoxy group, and $X_1$ represents an acid residue.

(c) When obtaining a compound of formula (I) wherein $R_2$ and $R_3$ together form a linear alkylene group having 4 to 7 carbon atoms which may be optionally substituted by a hydroxyl or hydroxymethyl group, and $R_4$ represents a hydrogen atom or a group of the formula $—R_5—Z$ in which $R_5$ is as defined hereinabove and Z represents the groups defined hereinabove excepting amino, lower alkanoyloxy, benzoyloxy and halobenzoyloxy groups, a compound of the following formula

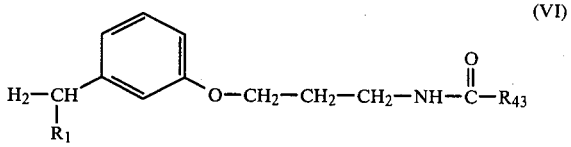 (VI)

wherein $R_1$ is as defined hereinabove, and $R_{43}$ represents a hydrogen atom or a group of the formula $—R_5—Z_3$ in which $R_5$ is as defined hereinabove and $Z_3$ represents the same groups as defined for symbol Z excepting amino, lower alkanoyloxy, benzoyloxy and halobenzoyloxy groups, is reacted with a compound of the formula

 (VII)

wherein $R_6$ represents a linear alkylene group having 4 to 7 carbon atoms which may be optionally substituted by a hydroxyl or hydroxymethyl group, and Hal represents a halogen atom.

(d) When obtaining a compound of formula (I) wherein $R_4$ represents a group of the formula $—R_5—Z$ in which $R_5$ is as defined hereinabove and Z represents a lower alkoxy, lower alkanoyloxy, benzoyloxy or halobenzoyloxy group, a compound of the following formula

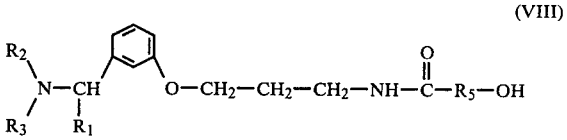 (VIII)

wherein $R_1$, $R_2$, $R_3$ and $R_5$ are as defined hereinabove, is reacted with a compound of the formula

 (IX)

wherein $R_7$ represents a lower alkyl group and $X_2$ represents an acid residue, or a carboxylic acid of the formula

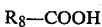 (X)

wherein $R_8$ represents a lower alkyl, phenyl, or halophenyl group, or its derivative.

(e) When obtaining a compound of formula (I) wherein $R_4$ represents a group of the formula $—R_5—Z$ in which $R_5$ is as defined hereinabove and Z represents an amino, mono- or di-(lower alkyl)amino, hydroxy lower alkylamino or lower alkanoylamino group, a compound of the following formula

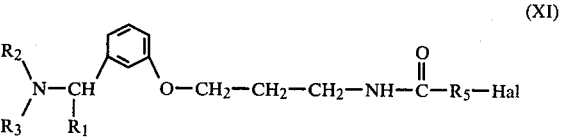 (XI)

wherein $R_1$, $R_2$, $R_3$ and $R_5$ are as defined hereinabove, and Hal represents a halogen atom, is reacted with an amine of the formula

wherein $R_9$ and $R_{10}$, independently from each other, represent a hydrogen atom or a lower alkyl group, or one of $R_9$ and $R_{10}$ represents a hydrogen atom and the other represents a hydroxy lower alkyl group or a lower alkanoyl group.

(f) If desired, the resulting compound of formula (I) is converted to its salt.

According to the embodiment (a) of the process of this invention, the amine compound of formula (II) or its reactive derivative is amidated by the carboxylic acid of formula (III) or its reactive derivative.

The reactive derivative of the amine compound (II) used as one starting material in the amidation reaction may be any of the those which are used to activate the amino group in amidation in the field of peptide chemistry. Examples are listed below.

(i) Isocyanates (or isothiocyanates)

(ii) Phosphazo compounds

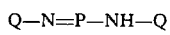

or

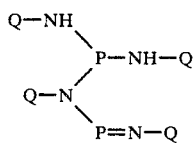

(iii) Phosphoroamidide compounds

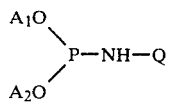

(iv) Phosphoroamidate compounds

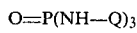

or

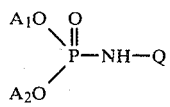

In each of the above formulae, Q represents the following

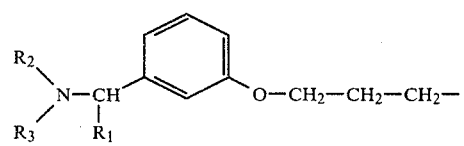

and $A_1$ and $A_2$ are identical or different, and each represents an alkyl, aryl or aralkyl group, or $A_1$ and $A_2$ together form an alkylene group or an o-phenylene group.

The carboxylic acid formula (III) used as the starting material in the aforesaid amidation reaction is a known compound. Its reactive derivative may be any of those which are used to activate the carboxyl group for amidation reaction in the field of peptide chemistry. Examples of the reactive derivative are shown below. When an amino group is present as the group $Z_1$ of the carboxylic acid (III), the amino group is desirably protected by a phthaloyl group, and when a hydroxyl group is present therein, the hydroxyl group may be protected by an acyl group. These protecting groups can be split off in a customary manner after the amidation reaction, for example by hydrazinolysis or mild hydrolysis.

(i) Acid halides

wherein E represents a halogen atom, especially chlorine or bromine, and $R_{41}$ is as defined hereinabove.

(ii) Esters

wherein $A_3$ represents a lower alkyl group, especially a methyl or ethyl group, or an active ester residue such as —CH$_2$CN,

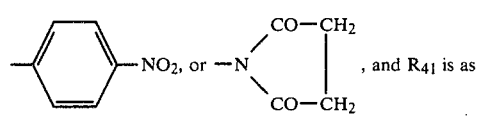

defined hereinabove.

(iii) Mixed acid anhydrides

wherein $A_4$ represents an organic or inorganic acid residue such as an acyl group (e.g., acetyl or propionyl), a group of the formula —COOA$_5$ (in which $A_5$ represents a lower alkyl group), or a group of the formula

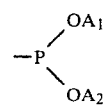

(in which $A_1$ and $A_2$ are as defined hereinabove), and $R_{41}$ is as defined hereinabove.

(iv) Active amides

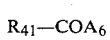

wherein $A_6$ represents a substituted or unsubstituted 1-imidazolyl or 1-pyrazolyl group, and $R_{41}$ is as defined hereinabove.

(v) Acid azides

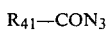

wherein $R_{41}$ is as defined hereinabove.

The amidation reaction between the amine compound (II) or its reactive derivative and the carboxylic acid (III) or its reactive derivative may be carried out by various known methods.

For example, it can be performed by direct condensation between the amine compound (II) and the carboxylic acid (III). The reaction may be carried out in the absence of solvent. Generally, it is preferred to carry out the reaction in an inert organic solvent, for example an aromatic hydrocarbon such as benzene, toluene or xylene, an ether such as tetrahydrofuran, dioxane, dimethoxyethane or diglyme, an amide such as dimethylformamide or dimethylacetamide, a halogenated hydrocarbon such as dichloromethane or chloroform, or dimethylsulfoxide. The reaction temperature and pressure are not particularly restricted, and can be varied widely depending upon the starting materials, etc. Usually, the reaction temperature is from about 0° C. to the refluxing temperature of the reaction mixture, preferably room temperature to 200° C., and the pressure is advantageously atmospheric pressure. If desired, the reaction may be carried out in the presence of a condensing agent. Examples of useful condensing agents are Lewis acids such as silicon tetrachloride, trichlorophenylsilane and titanium tetrachloride, N-ethyl-N!-diethylaminopropylcarbodiimide, N,N'-dicyclohexylcarbodiimide, a combination of a triaryl phosphine and a disulfide, and strong acid-type ion exchange resins such as Amberlite IR-120.

The amidation in accordance with this invention may also be carried out between the reactive derivative of the amine compound (II) and the free carboxylic acid (III), or between the free amine compound (II) and the reactive derivative of the carboxylic acid (III). This amidation can also be performed without a solvent, if required. Usually, it is advantageous to carry out this amidation in an inert organic solvent of the type exemplified hereinabove or in a high-boiling alcohol such as ethylene glycol or glycerol. The reaction temperature and pressure are not critical. Usually, the reaction temperature is from about −20° C. to the refluxing temperature of the reaction mixture, preferably from 0° C. to 180° C. The reaction pressure is advantageously atmospheric pressure.

In the aforesaid amidation reaction, the amount of the carboxylic acid (III) or its reactive derivative based on the amine (II) or its reactive derivative is not critical, and can be varied widely depending upon the type of the amidating agent. Generally, it is advantageous to use the carboxylic acid (III) or its reactive derivative in an amount of at least 1 mole, preferably 1 to 10 moles, more preferably 1 to 2 moles per mole of the compound (II) or its reactive derivative.

The compound of formula (II) used as one starting material in the aforesaid amidation reaction is a novel compound not described in the prior literature. It can be easily prepared, for example, by (1) reacting a compound of the following formula

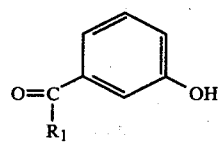

(XIII)

wherein $R_1$ is as defined hereinabove, with a compound of the following formula

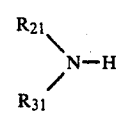

(XIV)

wherein $R_{21}$ and $R_{31}$ each represent a lower alkyl group, or together form a linear alkylene group having 4 to 7 carbon atoms, under reducing conditions, by the method described in German Laid-Open Pat. Publication No. 2,821,410 or a modification thereof, or (2) in accordance with the method (c) to be described hereinbelow, reacting a compound of the following formula

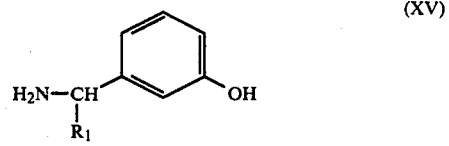

(XV)

wherein $R_1$ is as defined hereinabove, with a compound of the following formula

(VII)

wherein $R_6$ represents a linear alkylene group having 4 to 7 carbon atoms which may be optionally substituted by a hydroxyl or hydroxymethyl group, and Hal is as defined hereinabove, reacting the resulting compound of the following formula

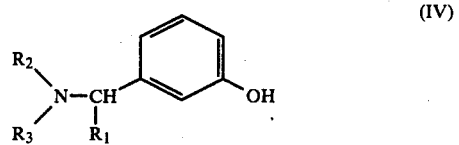

(IV)

wherein $R_1$, $R_2$ and $R_3$ are as defined hereinabove, in a manner known per se (for example, the method described in German Laid-Open Pat. Publication No. 2,821,410) with a compound of the following formula

(XVI)

wherein Hal represents a halogen atom, and B represents a protected amino group, such as a phthalimide group, and then splitting off the protecting group.

The resulting compound of formula (II) can be converted into its reactive derivative in a customary manner in the peptide chemistry.

The reaction between the phenol derivative of formula (IV) and the propylamide derivative of formula (V) in accordance with the process embodiment (b) of this invention can be performed by reacting the phenol derivative (IV) in the form of phenolate with the propylamide derivative (V), or reacting the phenol derivative (IV) with the propylamide derivative (V) in the presence of a base.

The phenolate of the phenol derivative (IV) is expressed by the following formula

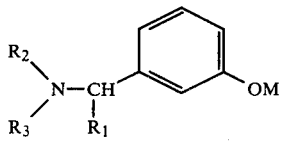

(IV-a)

wherein $R_1$, $R_2$ and $R_3$ are as defined hereinabove, and M represents an alkali metal.

Examples of the base mentioned above include sodium carbonate, potassium carbonate, sodium hydroxide, potassium hydroxide, sodium hydride, sodium azide, and sodium amide. The base can be used in an amount of at least 1 equivalent, preferably 1 to 5 equivalents, more preferably 1 to 1.5 equivalents per mole of the phenol derivative (IV).

The reaction of the phenol derivative (IV) or the phenolate (IV-a) with the propylamide derivative (V) can be performed in the absence of a solvent or in the presence of an inert solvent, for example water, an alcohol such as methanol, ethanol or butanol, a ketone such as acetone, or methyl ethyl ketone, an aromatic hydrocarbon such as benzene or toluene, an amide such as dimethylformamide or dimethylacetamide, or dimethylsulfoxide. The reaction temperature is not critical, and can be varied widely depending upon the type of the starting materials, etc. Generally, the suitable reaction temperature is from room temperature to the refluxing temperature of the reaction mixture, preferably from about 20° C. to the refluxing temperature of the reaction mixture.

The amount of the propylamide derivative (V) based on the phenol derivative (IV) [phenolate of formula (IV-a] is neither critical, and can be varied widely. Generally, the amount of the propylamide derivative (V) is at least 1 mole, preferably 1 to 10 moles, more preferably 1 to 2 moles per mole of the phenol derivative (IV).

The acid residue for $X_1$ in formula (V) includes, for example, halogen atoms (e.g., chlorine, bromine or iodine), and organic sulfonyloxy groups such as methanesulfonyloxy and tosyloxy groups. Of these, the halogen atoms are preferred.

According to the embodiment (c) of the process of this invention, the compound of formula (VI) is reacted with the dihalide compound of formula (VII).

The reaction of the compound (VI) with the compound (VII) is carried out generally in an inert organic solvent, for example, an ether such as ethyl ether, tetrahydrofuran or dioxane, an aromatic hydrocarbon such as benzene or toluene, an amide such as dimethylformamide or dimethylacetamide, or dimethylsulfoxide, preferably in the presence of an acid binder. Examples of useful acid binder are aliphatic tertiary amines such as trimethylamine or triethylamine, and inorganic bases such as sodium hydroxide, potassium hydroxide, sodium carbonate and potassium carbonate. Advantageously, the acid binder is used in an amount of about 1 to about 3 moles per mole of the compound (VI).

The amount of the compound (VII) used in the above is generally 1 to 5 moles, preferably 1 to 2 moles per mole of the compound (VI).

The reaction temperature and pressure are not critical, and can be varied widely depending upon the starting materials, the solvent, etc. Usually, the reaction temperature is from about 0° C. to the refluxing temperature of the reaction mixture, preferably from room temperature to the refluxing temperature of the reaction mixture. Normal atmospheric pressure is sufficient as the reaction pressure.

The compound (VI) used as a starting material in the above reaction is also a novel compound not described in the prior literature. It can be prepared, for example, by reacting a compound of the following formula

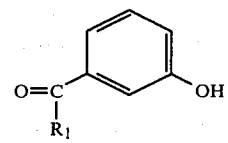

(XIII)

wherein $R_1$ is as defined hereinabove, with a compound of the following formula

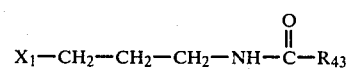

(XVII)

wherein $R_{43}$ and $X_1$ are as defined hereinabove, under similar conditions to the process embodiment (b) as described hereinabove to form a compound of the following formula

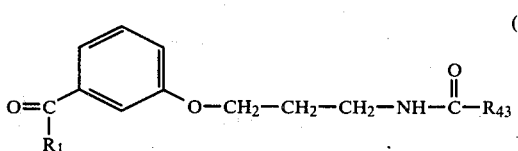

(XVIII)

wherein $R_1$ and $R_{43}$ are as defined hereinabove, reacting the resulting compound with hydroxylamine at a relatively low temperature of about 0° C. to room temperature in a suitable solvent such as an alcohol (e.g., methanol, ethanol or butanol) to convert it to an oxime of the following formula

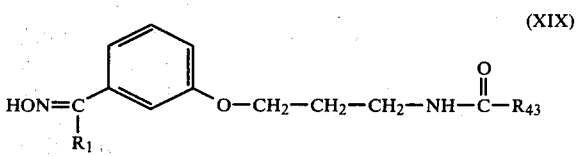

(XIX)

wherein $R_1$ and $R_{43}$ are as defined hereinabove, and then catalytically hydrogenating the resulting oxime (XIX) in a customary manner.

According to the embodiment (d) of the process of this invention, the compound of formula (VIII) is etherified or esterified with the compound of formula (IX) or the carboxylic acid of formula (X) or its reactive derivative. This etherification or esterification can be performed in accordance with usual methods.

The etherification of the compound (VIII) with the compound (IX) is usually carried out by reacting the compound (VIII) in the form of an alcoholate with the compound (IX).

The alcoholate of the compound of formula (VIII) can generally be represented by the following formula

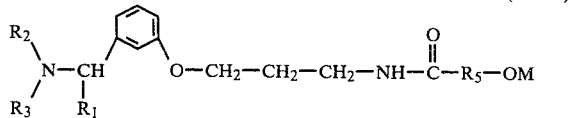

(VIII-a)

wherein $R_1$, $R_2$, $R_3$ and $R_5$ are as defined hereinabove, and M represents an alkali metal such as sodium, potassium or lithium.

The alcoholate of formula (VIII-a) can be produced by reacting the compound (VIII) with a base such as sodium hydride or sodium amide. The alcoholate-forming reaction is usually carried out in an inert organic solvent such as an amide (e.g., dimethylformamide or dimethylacetamide), or dimethylsulfoxide at a temperature of generally from $-10°$ C. to room temperature using at least 1 equivalent, preferably 1 to 1.5 equivalents, of the base per mole of the compound of formula (VIII).

The reaction of the resulting alcoholate (VIII-a) with the compound (IX) can be carried out in the absence of a solvent, or in an inert organic solvent, for example an aromatic hydrocarbon such as benzene or toluene, an amide such as dimethylformamide or dimethylacetamide, or dimethylsulfoxide. The reaction temperature is not critical, and can be varied widely depending upon the type of the starting materials, etc. Generally, the suitable reaction temperature is from about $-10°$ C. to the refluxing temperature of the reaction mixture, preferably from $0°$ C. to room temperature. Under these reaction conditions, the reaction can be completed in about 5 minutes to about 1 hour.

The amount of the compound (IX) based on the alcoholate (VIII-a) is not critical, and can be varied widely. Advantageously, the compound of formula (IX) is used in an amount of generally at least 1 mole, preferably 1 to 10 moles, more preferably 1 to 2 moles per mole of the alcoholate (VIII-a).

The acid residue for $X_2$ in the compound (IX) used as a starting material includes, for example, halogen atoms (e.g., chlorine, bromine or iodine), and organic sulfonyloxy groups such as methanesulfonyloxy and tosyloxy groups. Of these, the halogen atoms are preferred.

Specific examples of the compound (IX) are methyl iodide, ethyl iodide, etyyl bromide and propyl iodide.

The esterification reaction of the compound (VIII) with the carboxylic acid (X) or its reactive derivative [this reactive derivative includes those exemplified hereinabove with regard to formula (III)] can be carried out in accordance with various known methods.

For example, the esterification reaction can be performed by direct condensation between the compound (VIII) and the carboxylic acid (X). Preferably, the reaction is carried out between the compound (VIII) and the reactive derivative of the carboxylic acid (X). The reaction may be carried out in the absence of a solvent. Advantageously, the reaction is generally carried out in an inert organic solvent. Suitable solvents include amines such as pyridine and triethylamine, aromatic hydrocarbons such as benzene, toluene and xylene, ethers such as tetrahydrofuran, dioxane, dimethoxyethane and diglyme, amides such as dimethylformamide and dimethylacetamide, halogenated hydrocarbons such as dichloromethane and chloroform, and dimethylsulfoxide. The reaction temperature and pressure are not critical. Usually, the reaction temperature is from about $-20°$ C. to the refluxing temperature of the reaction mixture, preferably from $0°$ C. to $180°$ C. The reaction pressure is advantageously atmospheric pressure.

In the above esterification reaction, the amount of the carboxylic acid (X) or its reactive derivative based on the compound (VIII) is neither critical, and can be varied widely depending upon the type of the compound (X) used. Advantageously, the amount of the carboxylic acid (X) or its reactive derivative is generally at least 1 mole, preferably 1 to 10 moles, more preferably 1 to 2 moles per mole of the compound (VIII).

The compound (VIII) used as a starting material in the embodiment (d) is among the compounds of formula (I) of this invention, and can be prepared in accordance with the embodiment (a) or (c) of the process of this invention.

According to the embodiment (e) of the process of this invention, the compound of formula (XI) is reacted with the amine of formula (XII).

This reaction is generally carried out in an inert organic solvent, for example an ether such as ethyl ether, tetrahydrofuran or dioxane, an aromatic hydrocarbon such as benzene or toluene, an amide such as dimethylformamide or dimethylacetamide, or dimethylsulfoxide, preferably in the presence of an acid binder of the type exemplified hereinabove with regard to the process embodiment (c). The acid binder is used advantageously in an amount of about 1 to about 3 moles per mole of the compound (XI).

In the above reaction, the amine of formula (XII) is used generally in an amount of 1 to 50 moles, preferably 3 to 20 moles per mole of the compound (XI).

The reaction temperature and pressure are not critical, and can be varied widely depending upon the reactants and the solvent used, etc. The reaction is advantageously carried out at a temperature of generally from about $0°$ C. to the refluxing temperature of the reaction mixture, preferably from room temperature to the refluxing temperature of the reaction mixture, under normal atmospheric pressure.

The compound (XI) used as a starting material in embodiment (e) is a novel compound not described in the prior literature. It can be prepared, for example, by the process embodiment (a) using a carboxylic acid corresponding to formula (III) in which $Z_1$ is a halogen atom instead of the carboxylic acid (III) used in embodiment (a).

The compound (I) produced by the process of this invention described hereinabove can be converted to the corresponding salt in accordance with the process embodiment (f). The salt-forming reaction can be easily performed in a customary manner by treating the compound (I) with an inorganic or organic acid.

Thus, the compound of formula (I) or its salt obtained by the process of this invention can be isolated from the reaction mixture and/or purified by various known means, such as recrystallization, distillation, column chromatography, and thin-layer chromatography.

The substituted phenoxypropylamine compounds of formula (I) and the salts thereof have the action of inhibiting secretion of gastric acid based on their antagonistic action against histamine $H_2$ receptors, and are useful for treating diseases caused by gastric acid, for example gastric or duodenal ulcers.

The superior histamine $H_2$ receptor antagonizing activity of the compounds of formula (I) can be demonstrated by the following animal experiment.

The compounds of this invention used in the following animal experiment are abbreviated as follows:

A: N-[3-[3-[1-(1-Pyrrolidinyl)ethyl]phenoxy]propyl]-formamide.

B: N-[3-[3-[1-Pyrrolidinyl)propyl]phenoxy]-propyl]-formamide.

C: N-[3-[3-(1-Piperidinylmethyl)phenoxy]propyl]formamide.

D: N-[3-[3-(1-(1-Perhydroazepinyl)ethyl]phenoxy]-propyl]formamide.

E: N-[3-[3-[1-(3-Hydroxy)pyrrolidinyl]ethyl]phenoxy]propyl]formamide.

F: N-[3-[3-[1-(1-Pyrrolidinyl)ethyl]phenoxy]propyl]acetamide.

G: N-[3-[3-[1-(1-Pyrrolidinyl)propyl]phenoxy]-propyl]acetamide.

H: N-[3-[3-(1-Piperidinylmethyl)phenoxy]propyl]acetamide.

I: N-[3-[3-[1-(1-Piperidinyl)ethyl]phenoxy]propyl]acetamide.

J: N-[3-[3-[1-(1-Pyrrolidinyl)ethyl]phenoxy]propyl]-propionamide.

K: N-[3-[3-[1-(1-Pyrrolidinyl)ethyl]phenoxy]propyl]-hydroxyacetamide.

L: N-[3-[3-(1-Piperidinylmethyl)phenoxy]propyl]hydroxyacetamide.

M: N-[3-[3-(1-Perhydroazepinylmethyl)phenoxy]-propyl]hydroxyacetamide.

N: N-(3-Aminopropionyl)-3-[3-[1-(1-pyrrolidinyl)ethyl]phenoxy]propylamine.

O: N-[3-[3-(1-Piperidinylmethyl)phenoxy]propyl]methoxyacetamide.

P: N-[3-[3-[1-(1-Pyrrolidinyl)ethyl]phenoxy]propyl]acetoxyacetamide.

Q: N-[3-[3-(1-Piperidinylmethyl)phenoxy]propyl]acetoxyacetamide.

R: N-[3-[3-(1-Perhydroazepinylmethyl)phenoxy]-propyl]acetoxyacetamide.

S: N-[3-[3-(1-Piperidinylmethyl)phenoxy]propyl]propionyloxyacetamide.

T: N-[3-[3-(1-Piperidinylmethyl)phenoxy]propyl]-benzoyloxyacetamide.

U: N-(3,4-Dichlorobenzoyloxyacetyl)-3-[3-(1-perhydroazepinylmethyl)phenoxy]propylamine.

(1) Measurement of histamine $H_2$ receptor antagonizing activity

A guinea pig, Hartley, (male 400–550 g) was struck at the head to let out blood, and the heart was enucleated. The right atrium was separated in a Tyrod solution saturated with oxygen, and a silk thread was attached to its both ends. Using the silk threads at both ends, the atrium was suspended under a tension of 700 mg in a Magnus tube (25 ml) containing a Tyrod solution maintained at 36° C. through which mixture of 95% of $O_2$ and 5% of $CO_2$ was passed. The contracting motion of the atrium was recorded by a force-displacement transducer, and the number of heart beats was calculated.

Histamine (used in the form of diphosphate; the same hereinbelow) was cumulatively added to the Magnus tube in a concentration of $1 \times 10^{-8}$ M to $1 \times 10^{-4}$ M in such an amount that the logarithm of the amount provides an equal interval of ½, until a maximum increase in heart beat was obtained. Thus, the dose-response curve of histamine was obtained. The inside of the Magnus tube was washed several times with a Tyrod solution, and the atrium was stabilized for 1 hour. Then, the above procedure was repeated to obtain the dose-response curve of histamine again. The inside of the Magnus tube was washed several times, and the tissues were stabilized for 50 minutes. Then, a test compound ($1 \times 10^{-5}$ M) was added to the Magnus tube, and after 20 minutes, the dose-response curve of histamine in the presence of the test compound was obtained.

The $PA_2$ value (the negative logarithm of the molar concentration of the test compound required to double the concentration of histamine in the Magnus tube required to induce a certain reaction) was calculated from the dose-response curve of histamine obtained in the second operation and the dose-response curve of histamine in the presence of the test compound in accordance with the method of J. M. Van Rossum (Arch. int. Pharmacodyn., 143, 299, 1963). The results are shown in Table 1.

TABLE 1

| Compound | $PA_2$ |
|---|---|
| A | 6.12 |
| B | 6.49 |
| C | 6.50 |
| D | 6.14 |
| E | 5.99 |
| F | 6.16 |
| G | 6.47 |
| H | 6.52 |
| I | 5.97 |
| J | 6.04 |
| K | 5.83 |
| L | 6.79 |
| M | 6.29 |
| N | 6.26 |
| O | 6.62 |
| P | 6.11 |
| Q | 7.10 |
| R | 6.28 |
| S | 6.77 |
| T | 6.74 |
| U | 6.80 |

(2) Toxicity

A 5% Tween 80 suspension of a test compound was orally administered to groups of ddY mice (male: 19–22 g), each consisting of 5 mice, and the animals were observed for 72 hours. The $LD_{50}$ values of the test compounds calculated by the Litchfield-Wilcoxon method based on the results of the observation were as follows:

(i) $LD_{50}$ of compound A: 2500 mg/kg (ii) $LD_{50}$ of compound F: 2100 mg/kg (iii) $LD_{50}$ of compound Q: 1000 mg/kg Thus, the compound of formula (I) of this invention can be administered as an antiulcer agent orally or parenterally (e.g., intramuscularly, intravenously, subcutaneously, intrarectally, intradermally, etc.) for the treatment and medication of men and other warm-blooded animals.

When the compound of this invention is used as a drug, it can be formulated into various forms suitable for oral or parenteral administration. The compounds of this invention can be formulated by using various non-toxic additives normally used in drugs of this kind, such as excipients, binders, lubricants, disintegrating agents, antiseptics, isotonic agents, stabilizers, dispersing agents, antioxidants, coloring agents, flavoring agents, and buffers.

Depending upon the end uses, these drugs can be prepared into a solid form (e.g., tablets, hard capsules, soft capsules, granules, powders, pellets, pills, trouches, etc.), a semi-solid form (e.g., suppositories, ointment, etc.) and a liquid form (injections, emulsions, suspension, syrups, sprays, etc.). Specific examples of the non-toxic additives include gelatin, starch, glucose, lactose, fructose, maltose, magnesium carbonate, talc, magnesium stearate, methyl cellulose, carboxy methyl cellulose or the salts thereof, gum arabic, polyethylene glycol, alkyl p-hydroxybenzoates, syrup, ethanol, propylene glycol, vaseline, carbowax, glycerol, sodium chloride, sodium sulfite, sodium phosphate, and nitric acid.

The above drugs may also contain other therapeutically effective agents.

The content of the compound of this invention in the drug differs depending upon its preparation form. Desirably, it is about 5 to 100% by weight in solid and semi-solid formulations, and about 0.1 to 10% by weight in liquid formulations.

The dosage of the compound of this invention can be varied widely depending upon the subject to which it is to be administered (man or other warm-blooded animals), the route of administration, the condition of the patient, the diagnosis of a physician, etc. Generally the dosage is 0.2 to 20 mg/kg, preferably 0.5 to 10 mg/kg, per day. Larger or smaller dosages may be possible depending upon the condition of the patient and the diagnosis of a physician. The aforesaid dosage may be administered once or several times a day.

The following Examples illustrate the present invention more specifically.

EXAMPLE 1

A mixture of 1 g of 3-[3-(1-piperidinylmethyl)phenoxy]propylamine, 1 g of sodium formate and 3 ml of formic acid was refluxed for 1 hour, and a greater portion of the solvent was distilled off under reduced pressure, and water was added to the residue. The mixture was alkalized with 4% sodium hydroxide solution. The product was extracted with chloroform. The extract was dried over anhydrous magnesium sulfate. The solvent was distilled off, and the residue was separated and purified by thin-layer chromatography (TLC) (developing solvent: chloroform/methanol=9/1) to afford 436 mg of N-[3-[3-(1-piperidinylmethyl)phenoxy]propyl]formamide as an oil.

IR(film, cm$^{-1}$): 3282, 1632. NMR(CDCl$_3$, δ): 1.30–1.70 (6H, m.), 2.04 (2H, q., J=6 Hz), 2.30–2.50 (4H, m.), 3.15 (1H, s.), 3.43 (2H, s.), 3.53 (2H, t., J=6 Hz), 4.01 (2H, t., J=6 Hz), 6.70–7.30 (4H, m.), 8.13 (1H, s.).

The above reaction was repeated using suitable amines to give the following compounds.

(i) N-[3-[3-[1-(1-Piperidinyl)ethyl]phenoxy]propyl]formamide

IR(film, cm$^{-1}$): 3310, 1670. NMR(CDCl$_3$, δ): 1.34 (3H, d., J=7 Hz), 1.35–1.75 (6H, m.), 2.05 (2H, q., J=6 Hz), 2.30–2.55 (4H, m.), 3.04 (1H, q., J=7 Hz), 3.30–3.70 (3H, m.), 4.40 (2H, t., J=6 Hz), 6.65–7.30 (5H, m.), 8.15 (1H, broad s.).

(ii) N-[3-[3-(1-Perhydroazepinylmethyl)phenoxy]propyl]formamide

IR(film, cm$^{-1}$): 3800, 1670. NMR(CDCl$_3$, δ): 1.4–2.8 (10H, m.), 2.4–2.8 (4H, m.), 3.3–3.7 (2H, m.), 3.59 (2H, s.), 4.02 (2H, t., J=6 Hz), 6.6–7.4 (4H, m.), 8.13 (1H, s.).

(iii) N-[3-[3-[1-(1-Perhydroazepinyl)ethyl]phenoxy]propyl]formamide

IR(film, cm$^{-1}$): 1670. NMR(CDCl$_3$, δ): 1.35 (3H, d., J=7 Hz), 1.6 (8H, m.), 2.01 (2H, m., J=7 Hz), 2.68 (4H, m.), 3.3–3.9 (3H, m.), 4.05 (2H, t., J=7 Hz), 6.35 (1H, broad s.), 6.4–7.4 (4H, m.), 8.18 (1H, broad s.).

(iv) N-[3-[3-(1-Perhydroazocinylmethyl)phenoxy]propyl]formamide

IR(film, cm$^{-1}$): 1660. NMR(CDCl$_3$, δ): 1.62 (10H, m.), 1.99 (2H, m., J=6 Hz), 2.56 (4H, m.), 3.2–3.7 (4H, m.), 4.02 (2H, t., J=6 Hz), 6.3 (1H, broad s.), 6.4–7.4 (4H, m.), 8.12 (1H, broad s.).

(v) N-[3-[3-[1-(1-Perhydroazocinyl)ethyl]phenoxy]propyl]formamide

IR(film, cm$^{-1}$): 1670. NMR(CDCl$_3$, δ): 1.24 (3H, d., J=7 Hz), 1.6 (10H, m.), 2.00 (2H, m., J=7 Hz), 2.5 (4H, m.), 3.2–3.8 (3H, m.), 4.02 (2H, t., J=7 Hz), 6.4 (1H, broad s.), 6.4–7.4 (4H, m.), 8.12 (1H, broad s.).

(vi) N-[3-[3-[1-(3-Hydroxy)pyrrolidinylmethyl]phenoxy]propyl]formamide

IR(film, cm$^{-1}$): 3300, 1660. NMR(CDCl$_3$, δ): 1.6–3.1 (9H, m.), 3.43 (2H, t., J=6.5 Hz), 3.62 (2H, s.), 4.03 (2H, t., J=6 Hz), 4.35 (1H, m.), 6.6–7.4 (5H, m.), 8.15 (1H, broad s.).

(vii) N-[3-[3-[1-[1-(3-Hydroxy)pyrrolidinyl]ethyl]phenoxy]propyl]formamide

IR(film, cm$^{-1}$): 3300, 1670. NMR(CDCl$_3$, δ): 1.35 (3H, d., J=7 Hz), 1.7–3.0 (8H, m.), 3.1–3.6 (4H, m.), 4.01 (2H, t., J=6 Hz), 4.3 (1H, m.), 6.4–7.3 (5H, m.), 8.11 (1H, broad s.).

(viii) N-[3-[3-[1-(3-Hydroxy)piperidinylmethyl]phenoxy]propyl]formamide

IR(film, cm$^{-1}$): 3320, 1675. NMR(CDCl$_3$, δ): 1.6 (4H, m.), 1.98 (2H, m., J=6 Hz), 2.3–2.6 (4H, m.), 2.88 (1H, broad s.), 3.46 (2H, s.), 3.46 (2H, m.), 3.8 (1H, m.), 4.01 (2H, t., J=6 Hz), 6.3 (1H, m.), 6.6–7.3 (4H, m.), 8.11 (1H, broad s.).

(ix) N-[3-[3-[1-(3-Hydroxymethyl)piperidinylmethyl]phenoxy]propyl]formamide

IR(film, cm$^{-1}$): 3300, 1670. NMR(CDCl$_3$, δ): 1.2–3.0 (12H, m.), 3.48 (2H, s.), 3.3–3.6 (4H, m.), 4.04 (2H, t., J=6 Hz), 6.4 (1H, m.), 6.7–7.3 (4H, m.), 8.12 (1H, broad s.).

(x) N-[3-[3-[1-Pyrrolidinyl)propyl]phenoxy]propyl]foramide

IR(film, cm$^{-1}$): 3300, 1670. NMR(CDCl$_3$, δ): 0.67 (3H, t., J=7 Hz), 1.60–2.20 (8H, m.), 2.30–2.80 (4H, m.), 2.99 (1H, q., J=5 Hz), 3.3–3.7 (2H, m.), 4.05 (2H, t., J=6 Hz), 6.6–7.4 (4H, m.), 8.16 (1H, s.).

(xi) N-[3-[3-[1-(1-Pyrrolidinyl)ethyl]phenoxy]propyl]formamide

IR(film, cm$^{-1}$): 1680. NMR(CDCl$_3$, δ): 1.36 (3H, d., J=6 Hz), 1.5–2.8 (10H, m.), 3.15 (1H, q., J=6 Hz), 3.50 (2H, q., J=6 Hz), 4.03 (2H, t., J=6 Hz), 6.6–7.4 (4H, m.), 8.15 (1H, broad s.).

(xii) N-[3-[3-(1-Pyrrolidinylmethyl)phenoxy]propyl]formamide

IR(film, cm$^{-1}$): 3300, 1680. NMR(CDCl$_3$, δ): 1.50–2.25 (6H, m.), 2.30–2.84 (4H, m.), 3.50 (2H, q., J=6 Hz), 3.58 (2H, s.), 4.03 (2H, t., J=6 Hz), 6.60–7.50 (4H, m.), 8.15 (1H, s.).

(xiii) N-[3-(3-Dimethylaminomethylphenoxy)propyl]formamide

IR(film, cm$^{-1}$): 3300, 1680. NMR(CDCl$_3$, δ): 1.7–2.2 (2H, m.), 2.25 (6H, s.), 3.40 (2H, s.), 3.46 (2H, q., J=6 Hz), 4.03 (2H, t., J=6 Hz), 6.65–7.40 (4H, m.), 8.14 (1H, s.).

EXAMPLE 2

One gram of 3-[3-(1-piperidinylmethyl)phenoxy]propylamine was dissolved in 1 ml of pyridine, and 0.5 ml of acetic anhydride was added. The mixture was allowed to stand at room temperature for 4 hours. The solvent was distilled off under reduced pressure, and small amounts of water and potassium carbonate were added. The mixture was extracted with chloroform, washed with water, and dried. Then, the solvent was distilled off. The residue was purified by TLC (developing solvent: chloroform/methanol=9/1) to afford 753 mg of N-[3-[3-(1-piperidinylmethyl)phenoxy]propyl] acetamide as an oil.

IR(film, cm$^{-1}$): 3285, 1662. NMR(CDCl$_3$, δ): 1.40–1.75 (6H, m.), 1.96 (3H, s.), 2.01 (2H, q., J=6 Hz), 2.25–2.50 (4H, m.), 3.42 (2H, s.), 3.48 (2H, t., J=6 Hz), 4.03 (2H, t., J=6 Hz), 6.00 (1H, s.), 6.71–7.32 (4H, m.).

The following compounds were obtained by repeating the above reaction using suitable amines.

N-[3-[3-[1-(1-Piperidinyl)ethyl]phenoxy]propyl]acetamide

IR(film, cm$^{-1}$): 3300, 1645. NMR(CDCl$_3$, δ): 1.36 (3H, d., J=7 Hz), 1.25–1.75 (6H, m.), 1.97 (3H, s.), 2.05 (2H, q., J=6 Hz), 2.30–2.55 (4H, m.), 3.20–3.60 (3H, m.), 4.03 (2H, t., J=6 Hz), 6.38 (1H, broad s.), 6.60–7.35 (4H, m.).

(ii) N-[3-[3-[1-(1-Pyrrolidinyl)propyl]phenoxy]propyl]acetamide

IR(film, cm$^{-1}$): 3300, 1660. NMR(CDCl$_3$, δ): 0.65 (3H, t., J=7 Hz), 1.50–2.20 (8H, m.), 1.96 (3H, s.), 2.23–2.90 (4H, m.), 2.99 (1H, q., J=5 Hz), 3.2–3.6 (2H, m.), 4.02 (2H, t., J=6 Hz), 6.6–7.4 (4H, m.).

(iii) N-[3-[3-[1-(1-Pyrrolidinyl)ethyl]phenoxy]propyl]acetamide

IR(film, cm$^{-1}$): 1660. NMR(CD$_3$OD, δ): 1.36 (3H, d., J=6 Hz), 1.5–2.8 (10H, m.), 1.93 (3H, s.), 3.19 (1H, q., J=6 Hz), 3.34 (2H, t., J=6 Hz), 4.00 (2H, t., J=6 Hz), 6.6–7.4 (4H, m.).

(iv) N-[3-[3-(1-Pyrrolidinylmethyl)phenoxy]propyl]acetamide

IR(film, cm$^{-1}$): 3300, 1660. NMR(CDCl$_3$, δ): 1.60–2.25 (6H, m.), 1.96 (3H, s.), 2.3–2.9 (4H, m.), 3.44 (2H, q., J=6 Hz), 3.58 (2H, s.), 4.03 (2H, t., J=6 Hz), 6.65–7.60 (4H, m.).

(v) N-[3-(3-Diethylaminomethylphenoxy)propyl] acetamide

IR(film, cm$^{-1}$): 1653. NMR(CDCl$_3$, δ): 1.03 (6H, t.), 1.96 (3H, s.), 2.02 (2H, m.), 2.54 (4H, q.), 3.38 (2H, t.), 3.53 (2H, s.), 4.02 (2H, t.), 6.6–7.4 (4H, m.).

(vi) N-(3-Acetylaminopropionyl)-3-[3-[1-(1-pyrrolidinyl]ethyl]phenoxy]propylamine IR(film, cm$^{-1}$): 1660. NMR(CD$_3$OD, δ): 1.59 (3H, d., J=6.5 Hz), 1.90 (3H, s.), 1.8–2.2 (2H, t., J=6 Hz), 2.7–3.6 (7H, m.), 4.0 (2H, m.), 6.8–7.5 (4H, m.).

EXAMPLE 3

130 mg of 3-[3-[1-(3-hydroxy)pyrrolidinylmethyl]phenoxy]propylamine was dissolved in 1 ml of pyridine, and 57 mg of acetic anhydride was added. The mixture was refluxed for 30 minutes. Under reduced pressure, the solvent was distilled off, and small amounts of water and potassium carbonate were added. The mixture was extracted with chloroform, and dried over anhydrous magnesium sulfate. The solvent was distilled off. The residue was purified by TLC (developing solvent: chloroform/methanol=9/1) to afford 52 mg of N-[3-[3-[1-(3-hydroxy)pyrrolidinylmethyl]phenoxy]propyl] acetamide as an oil.

IR(film, cm$^{-1}$): 3300, 1650. NMR(CDCl$_3$, δ): 1.96 (3H, s.), 1.6–3.1 (8H, m.), 3.4 (3H, m.), 3.60 (2H, s.), 4.01 (2H, t., J=6 Hz), 4.3 (1H, m.), 6.4 (1H, m.), 6.6–7.4 (4H, m.).

The following compounds were obtained by repeating the above reaction using suitable amines.

(i) N-[3-[3-[1-[1-(3-Hydroxy)pyrrolidinyl]ethyl]phenoxy]propyl]acetamide

IR(film, cm$^{-1}$): 3300, 1655. NMR(CDCl$_3$, δ): 1.86 (3H, d., J=7 Hz), 1.97 (3H, s.), 1.70–3.0 (9H, m.), 3.1–3.6 (3H, m.), 4.01 (2H, t.), 4.3 (1H, m.), 6.1 (1H, m.), 6.7–7.3 (4H, m.).

(ii) N-[3-[3-[1-(3-Hydroxy)piperidinylmethyl]phenoxy]propyl]acetamide

IR(film, cm$^{-1}$): 3300, 1660. NMR(CDCl$_3$, δ): 1.6 (4H, m.), 1.94 (3H, s.), 1.8–2.8 (7H, m.), 3.38 (2H, t., J=6 Hz), 3.47 (2H, s.), 3.8 (1H, m.), 4.02 (2H, t., J=6 Hz), 6.1 (1H, m.), 6.7–7.3 (4H, m.).

EXAMPLE 4

211.8 mg of 3-[3-[1-(1-pyrrolidinyl)ethyl]phenoxy]propylamine was dissolved in 2 ml of dry pyridine, and the solution was stirred under ice cooling. A solution of 87 mg of propionyl chloride in 2 ml of dry tetrahydrofuran was added dropwise in small portions. After the addition, the reaction temperature was adjusted to room temperature, and the mixturwe was stirred for 2 hours. The solvent was distilled off, and 10 ml of water was added. Furthermore, 300 mg of potassium carbonate was added. The precipitated oily product was extracted with 30 ml of chloroform. The extract was dried over anhydrous potassium carbonate, and the solvent was distilled off. The residue was purified by TLC (developing solvent: chloroform/methanol=9/1) to afford 185 mg of N-[3-[3-[1-(1-pyrrolidinyl)ethyl]phenoxy]propyl] propionamide as an oil.

IR(film, cm$^{-1}$): 1680. NMR(CDCl$_3$, δ): 1.13 (3H, t., J=7 Hz), 1.39 (3H, d., J=6 Hz), 1.5–2.8 (12H, m.), 3.18 (1H, q., J=6 Hz), 3.44 (2H, q., J=6 Hz), 4.03 (2H, t., J=6 Hz), 6.6–7.4 (4H, m.).

The following compounds were obtained by repeating the above reaction using suitable amines and acid chlorides.

(i) N-[3-(3-Dimethylaminomethylphenoxy)propyl]acetamide

IR(film, cm$^{-1}$): 3300, 1660. NMR(CDCl$_3$, δ): 1.96 (3H, s.), 1.74–2.20 (2H, m.), 2.24 (6H, s.), 3.39 (2H, s.), 3.44 (2H, q., J=6 Hz), 4.03 (2H, t., J=6 Hz), 6.64–7.40 (4H, m.).

(ii) N-[3-[3-[1-(1-Pyrrolidinyl)ethyl]phenoxy]propyl]pivalamide

IR(film, cm$^{-1}$): 3360, 2980, 1642. NMR(CDCl$_3$, δ): 1.19 (9H, s.), 1.36 (3H, d., J=7 Hz), 1.6–2.7 (10H, m.), 3.15 (1H, t., J=7 Hz), 3.50 (2H, t., J=6 Hz), 4.05 (2H, t., J=6 Hz), 6.2 (1H, m.), 6.6–7.3 (4H, m.).

EXAMPLE 5

1.59 g of 3-[3-(1-piperidinylmethyl)phenoxy]propylamine and 536 mg of hydroxyacetic acid were heated at 200° C. for 2 hours. The reaction mixture was cooled, and water was added. The mixture was alkalized with aqueous ammonia, and extracted with chloroform. The extract was dried over anhydrous sodium sulfate, and the solvent was distilled off to afford 1.86 g of N-[3-[3-(1-piperidinylmethyl)phenoxy]propyl]hydroxyacetamide.

Melting point: 170°–172° C. (oxalate). IR(film, cm$^{-1}$): 3410, 3290, 1660. NMR(CDCl$_3$, δ): 1.20–1.75 (6H, m.), 1.84 (2H, q., J=6 Hz), 2.30–2.60 (4H, m.), 3.40 (2H, s.), 3.50 (2H, t., J=6 Hz), 3.98 (2H, s.), 4.00 (2H, t., J=6 Hz), 5.29 (1H, s.), 6.50–7.30 (5H, m.).

The following compounds were obtained by repeating the above reaction using suitable amines and acids.

N-[3-[3-[1-(1-Piperidinyl)ethyl]phenoxy]propyl]hydroxyacetamide

IR(film, cm⁻¹): 3380, 1654. NMR(CDCl₃, δ): 1.36 (3H, d., J=7 Hz), 1.20–1.75 (7H, m.), 2.02 (2H, q., J=6 Hz), 2.30–2.60 (4H, m.), 3.20–3.75 (3H, m.), 4.03 (2H, s.), 4.04 (2H, t., J=6 Hz), 5.09 (1H, broad s.), 6.65–7.40 (4H, m.).

(ii) N-[3-[3-(1-Perhydroazepinylmethyl)phenoxy]propyl]hydroxyacetamide

IR(film, cm⁻¹): 3400, 3300, 1660. NMR(CDCl₃, δ) 1.4–2.2 (10H, m.), 2.4–2.8 (4H, m), 3.3–3.7 (2H, m.), 3.60 (2H, s.), 4.00 (2H, s.), 4.03 (2H, t., J=6 Hz), 4.5–4.9 (1H, m.), 6.6–7.4 (4H, m.).

(iii) N-[3-[3-(1-Perhydroazocinylmethyl)phenoxy]propyl]hydroxyacetamide

IR(film, cm⁻¹): 1660. NMR(CDCl₃, δ):1.23 (10H, m.), 2.00 (2H, m., J=6 Hz), 2.6 (4H, m.), 3.3–3.7 (4H, m.), 4.02 (2H, s.), 4.03 (2H, t., J=6 Hz), 6.6–7.4 (4H, m.).

(iv) N-[3-[3-[1-[1-(3-Hydroxy)pyrrolidinyl]ethyl]phenoxy]propyl]hydroxyacetamide IR(film, cm⁻¹): 3360, 1660. NMR(CDCl₃, δ): 1.36 (3H, d., J=7 Hz), 1.7–3.0 (8H, m.), 3.1–3.7 (3H, m.), 3.82 (2H, s.), 3.8–4.0 (2H, m.), 4.05 (2H, t., J=6 Hz), 4.3 (1H, m.), 6.7–7.6 (5H, m.).

(v) N-[3-[3-[1-(3-Hydroxy)piperidinylmethyl]phenoxy]propyl]hydroxyacetamide

IR(film, cm⁻¹): 3400, 1650. NMR(CDCl₃, δ): 1.6 (4H, m.), 1.98 (2H, m., J=6 Hz), 2.3–2.6 (4H, m.), 3.49 (2H, s.), 3.8–4.0 (5H, m.), 3.99 (2H, s.), 4.05 (2H, t., J=6 Hz), 6.5–7.3 (5H, m.).

(vi) N-[3-[3-[1-(4-Hydroxy)piperidinylmethyl]phenoxy]propyl]hydroxyacetamide

IR(film, cm⁻¹): 3350, 1650. NMR(CDCl₃, δ): 1.5–2.4 (10H, m.), 2.7 (1H, m.), 3.45 (2H, s.), 3.3–3.7 (4H, m.), 3.99 (2H, s.), 4.05 (2H, t., J=6 Hz), 6.7–7.3 (5H, m.).

(vii) N-[3-[3-[1-(3-Hydroxymethyl)piperidinylmethyl]phenoxy]propyl]hydroxyacetamide IR(film, cm⁻¹): 3400, 1660. NMR(CDCl₃, δ): 1.2–3.0 (11H, m.), 3.46 (2H, s.), 3.3–3.7 (2H, m.), 3.9 (4H, broad s.), 4.00 (2H, s.), 4.07 (2H, t., J=6 Hz), 6.7–7.5 (5H, m.).

(viii) N-[3-[3-[1-(1-Pyrrolidinyl)ethyl]phenoxy]propyl]hydroxyacetamide

IR(film, cm⁻¹): 1660. NMR(CDCl₃, δ): 1.40 (3H, d., J=6 Hz), 1.5–2.9 (10H, m.), 3.20 (1H, q., J=6 Hz), 3.50 (2H, t., J=6 Hz), 4.06 (2H, s.), 4.06 (2H, t., J=6 Hz), 6.6–7.4 (4H, m.).

(ix) N-[3-[3-(1-Pyrrolidinylmethyl)phenoxy]propyl]hydroxyacetamide

IR(film, cm⁻¹): 3380, 3300, 1660. NMR(CDCl₃, δ): 1.5–2.8 (10H, m.), 3.46 (2H, q., J=6 Hz), 3.57 (2H, s.), 3.94 (2H, s.), 4.02 (2H, t., J=6 Hz), 6.6–7.4 (4H, m.).

(x) N-[3-(3-Dimethylaminomethylphenoxy)propyl]hydroxyacetamide

IR(film, cm⁻¹): 3350, 1650. NMR(CDCl₃, δ): 1.97 (2H, m., J=6.5 Hz), 2.25 (6H, s.), 3.37 (2H, s.), 3.46 (2H, q., J=6.5 Hz), 3.97 (2H, s.), 4.04 (2H, t., J=6.5 Hz), 6.6–7.5 (4H, m.).

(xi) N-[3-[3-[1-(1-Pyrrolidinyl)ethyl]phenoxy]propyl]phenoxyacetamide

IR(film, cm⁻¹): 1660. NMR(CDCl₃, δ): 1.36 (3H, d., J=7.0 Hz), 1.5–2.8 (10H, m.), 3.15 (1H, q., J=7.0 Hz), 3.56 (2H, q., J=6.0 Hz), 4.03 (2H, t., J=6.0 Hz), 4.48 (2H, s.), 6.5–7.5 (9H, m.).

(xii) N-[3-[3-(1-Piperidinylmethyl)phenoxy]propyl]phenoxyacetamide

IR(film, cm⁻¹): 3310, 1670. NMR(CDCl₃, δ): 1.2–1.8 (6H, m.), 2.00 (2H, m., J=6.0 Hz), 2.1–2.6 (4H, m.), 3.40 (2H, s.), 3.54 (2H, q., J=6.0 Hz), 4.00 (2H, t., J=6.0 Hz), 4.46 (2H, s.), 6.6–7.5 (9H, m.).

(xiii) N-(4-Chlorophenoxyacetyl)-3-[3-(1-piperidinylmethyl)phenoxy]propylamine

IR(film, cm⁻¹): 3300, 1670. NMR(CDCl₃, δ): 1.2–1.8 (6H, m.), 2.01 (2H, m., J=6.0 Hz), 2.2–2.6 (4H, m.), 3.42 (2H, s), 3.54 (2H, q., J=6.0 Hz), 4.02 (2H, t., J=6.0 Hz), 4.44 (2H, s.), 6.6–7.5 (8H, m.).

EXAMPLE 6

240 mg of 3-[3-[1-(1-pyrrolidinyl)ethyl]phenoxy]propylamine was dissolved in 4.5 ml of chloroform, and a solution of 144 mg of 3-hydroxypropionic acid in 0.5 ml of ethanol was added, followed by further addition of 300 mg of dicyclohexylcarbodiimide. The mixture was stirred at room temperature for 6 hours, and the solvent was distilled off under reduced pressure. The residue was purified by TLC (developing solvent: chloroform/methanol=9/1) to afford 180 mg of N-[3-[3-[1-(1-pyrrolidinyl)ethyl]phenoxy]propyl]hydroxypropionamide as an oil.

IR(film, cm⁻¹): 1660. NMR(CDCl₃, δ): 1.36 (3H, t., J=6 Hz), 1.5–2.9 (12H, m.), 3.15 (1H, q., J=6 Hz), 3.3–4.0 (4H, m.), 4.03 (2H, t., J=6 Hz), 6.6–7.4 (4H, m.).

The following compounds were obtained by repeating the above reaction using suitable acids.

(i) N-(4-Hydroxybutyryl)-3-[3-[1-(1-pyrrolidinyl)ethyl]phenoxy]propylamine

IR(film, cm⁻¹): 3300, 1650. NMR(CDCl₃, δ): 1.39 (3H, d., J=6.5 Hz), 1.6–2.2 (8H, m.), 2.2–2.8 (6H, m.), 3.17 (1H, q., J=6.5 Hz), 3.43 (2H, q., J=6 Hz), 3.64 (2H, t., J=6 Hz), 4.02 (2H, t., J=6 Hz), 6.6–7.4 (4H, m.).

(ii) N-[3-[3-[1-(1-Pyrrolidinyl)ethyl]phenoxy]propyl]isobutyramide

IR(film), cm⁻¹: 1680. NMR(CDCl₃, δ): 1.13 (6H, d., J=7 Hz), 1.37 (3H, d., J=6 Hz), 1.5–2.8 (10H, m.), 3.18 (1H, q., J=6 Hz), 3.45 (2H, q., J=6 Hz), 4.04 (2H, t., J=6 Hz), 6.6–7.3 (4H, m.).

(iii) N-[3-[3-[1(1-Pyrrolidinyl)ethyl]phenoxy]propyl]acetylaminoacetamide

IR(film, cm⁻¹): 1650. NMR(CD₃OD, δ): 1.37 (3H, d., J=6 Hz), 1.98 (3H, s.), 1.5–2.8 (10H, m.), 3.22 (1H, q., J=6 Hz), 3.35 (2H, q., J=6 Hz), 3.81 (2H, s.), 4.00 (2H, t., J=6 Hz), 6.6–7.4 (4H, m.).

EXAMPLE 7

(A) 180 mg of 3-[3-[1-(1-pyrrolidinyl)ethyl]phenoxy]propylamine, 200 mg of phthaloyl-β-alanine and 240 mg of dicyclohexylcarbodiimide were added to 25 ml of chloroform. The mixture was stirred at room temperature for 4 hours, and the solvent was distilled off under reduced pressure. The residue was separated and purified by TLC (developing solvent: chloroform/methanol=9/1) to afford 259.3 mg of N-[3-[3-[1-(1-pyrrolidinyl)ethyl]phenoxy]propyl]-3-phthaloyliminopropionamide as an oil.

NMR(CDCl₃, δ): 1.38 (3H, d., J=6 Hz), 1.5–2.8 (12H, m.), 3.19 (1H, q., J=6 Hz), 3.43 (2H, q., J=6 Hz), 3.99 (4H, t., J=6 Hz), 6.5–7.4 (4H, m.), 7.5–7.9 (4H, m.).

(B) 190 mg of the aminde compound obtained by step (A) and 0.5 ml of hydrazine hydrate were added to 6 ml of ethanol. The mixture was stirred at room temperature for 40 minutes. The insoluble matter was removed by filtration, and the solvent was distilled off under reduced pressure. The residue was separated and purified by TLC (developing solvent: chloroform/methanol=9/1) to afford 120 mg of N-(3-aminopropionyl)-

3-[3-[1-(1-pyrrolidinyl)ethyl]phenoxy]propylamine as an oil.

NMR(CDCl$_3$—D$_2$O, δ): 1.35 (3H, d., J=6 Hz), 1.5-2.8 (12H, m.), 297 (2H, t., J=6 Hz), 3.20 (1H, q., J=6 l Hz), 3.41 (2H, t., J=6 Hz), 4.00 (2H, t., J=6 Hz), 6.6-7.4 (4H, m.).

The following compounds were obtained by performing the above reactions in steps (A) and (B) using suitable amines and protected amino acids.

(i) N-Aminoacetyl-3-[3-[1-(1-pyrrolidinyl)ethyl]phenoxy]propylamine

IR(film, cm$^{-1}$): 1680. NMR(CDCl$_3$—D$_2$O, δ): 1.35 (3H, d., J=6 Hz), 1.5-2.8 (10H, m.), 3.0-3.8 (5H, m.), 4.02 (2H, t., J=6 Hz), 6.6-7.4 (4H, m.).

(ii); N-(3-Aminopropionyl)-3-[3-[1(1-piperidinyl)ethyl]phenoxy]propylamine

IR(film, cm$^{-1}$): 3400, 3280, 1650. NMR(CDCl$_3$, δ): 1.32 (3H, d., J=7 Hz), 1.15-2.70 (16H, m.), 2.80 (1H, q., J=7 Hz), 3.15-3.60 (4H, m.), 4.02 (2H, t., J=6 Hz), 6.70-7.40 (4H, m.).

(iii) N-(3-Aminopropionyl)-3-[3-(1-pyrrolidinylmethyl)phenoxy]propylamine dihydrochloride NMR(D$_2$O, δ): 1.6-2.9 (6H, m.), 2.5-2.9 (2H, m.), 3.0-3.9 (8H, m.), 4.14 (2H, t.), 4.36 (2H, s.), 6.9-7.7 (4H, m.).

(iv) N-(4-Aminobutyryl)-3-[3-[1-(1-pyrrolidinyl)ethyl]phenoxy]propylamine

IR(film, cm$^{-1}$): 3300, 1660. NMR(CDCl$_3$, δ): 1.35 (3H, d., J=6 Hz), 1.6-2.7 (16H, m.), 3.0-3.6 (5H, m.), 4.01 (2H, t., J=6 Hz), 6.6-7.3 (4H, m.).

EXAMPLE 8

300 mg of 3-[3-[1-(1-pyrrolidinyl)ethyl]phenoxy]propylamine was dissolved in 4.5 ml of pyrridine, and 350 mg of 2-phthaliminopropionyl chloride was added dropwise. The reaction solution was heated under reflux for 30 minutes, and the solvent was distilled off. The residue was purified by TLC (developing solvent: chloroform/methanol=9/1). The resulting oily product was subjected to hydrazinolysis in the same way as in Example 7 to afford 282 mg of N-(2-aminopropionyl)-3-[3-[1-(1-pyrrolidinyl)ethyl]phenoxy]propylamine.

IR(film, cm$^{-1}$): 1650. NMR(CDCl$_3$, δ): 1.30 (3H, d., J=6 Hz), 1.38 (3H, d., J=6 Hz), 1.6-2.8 (12H, m.), 3.0-3.8 (4H, m.), 4.02 (2H, t., J=6 Hz), 6.2-7.8 (5H, m.).

EXAMPLE 9

150 mg of N-[3-[3-[1-(1-pyrrolidinyl)ethyl]phenoxy]propyl]hydroxyacetamide was dissolved in 100 mg of acetic anhydride, and the solution was heated at 100° C. for 1 hour. Then, water was added, and the mixture was alkalized with aqueous ammonia. The mixture was extracted with ethyl acetate, and dried over anhydrous magnesium sulfate. The solvent was distilled off, and separated and purified by TLC (developing solvent: chloroform/methanol=9/1) to afford 115 mg of N-[3-[3-[1-(1-pyrrolidinyl)ethyl]phenoxy]propyl]acetoxyacetamide.

IR(film, cm$^{-1}$): 1755, 1670. NMR(CDCl$_3$, δ): 1.37 (3H, d., J=6.5 Hz), 1.6-2.8 (10H, m.), 2.14 (3H, s.), 3.17 (1H, q., J=6.5 Hz), 3.53 (2H, q., J=6.5 Hz), 4.05 (2H, t., J=6.5 Hz), 4.53 (2H, s.), 6.6-7.4 (4H, m.).

The following compounds were obtained by repeating the above reaction using suitable amindes and acid anhydrides.

(i) N-[3-[3-(1-Pyrrolidinylmethyl)phenoxy]propyl]acetoxyacetamide

IR(film, cm$^{-1}$): 1755, 1670. NMR(CDCl$_3$, δ): 1.4-2.8 (10H, m.), 2.13 (3H, s.), 3.54 (2H. q., J=6.5 Hz), 3.61 (2H, s.), 4.06 (2H, t., J=6.5 Hz), 4.54 (2H, s.), 6.6-7.4 (4H, m.).

(ii) N-[3-[3-(1-Piperidinylmethyl)phenoxy]propyl]acetoxyacetamide m.p.: 59°-60° C. (free), 145°-146° C. (HCl salt). IR(KBr, cm$^{-1}$): 3300, 1745, 1665. NMR(CDCl$_3$, δ): 1.2-2.6 (12H, m), 2.15 (3H, s.), 3.43 (2H, s.), 3.54 (2H, q., J=6.5 Hz), 4.06 (2H, t., J=6.5 Hz), 4.55 (2H, s.), 6.5-7.4 (4H, m.).

(iii) N-[3-[3-(1-Perhydroazepinylmethyl)phenoxy]propyl]acetoxyacetamide

IR(film, cm$^{-1}$): 3300, 1748, 1665. NMR(CDCl$_3$, δ): 1.4-2.3 (12H, m.), 2.12 (3H, s.), 2.4-2.8 (4H, m.), 3.51 (2H, q., J=6 Hz), 3.58 (2H, s.), 4.04 (2H, t., J=6 Hz), 4.52 (2H, s.), 6.6-7.3 (4H, m.).

(iv) N-[3-[3-(1-Piperidinylmethyl)phenoxy]propyl]propionyloxyacetamide m.p.: 38°-40° C. IR(film, cm$^{-1}$): 1755, 1675. NMR(CDCl$_3$, δ): 1.12 (3H, t., J=6.5 Hz), 1.3-2.7 (12H, m.), 3.41 (2H, s.), 3.50 (2H, q., J=6.5 Hz), 4.03 (2H, t., J=6.5 Hz), 4.53 (2H, s.), 6.6-7.4 (4H, m.).

(v) N-[3-[3-(1-Piperidinylmethyl)phenoxy]propyl]butyryloxyacetamide

IR(film, cm$^{-1}$): 3300, 1740, 1660. NMR(CDCl$_3$, δ): 0.93 (3H, t., J=7.0 Hz), 1.7-2.6 (16H, m.), 3.45 (2H, s.), 3.53 (2H, q., J=6.0 Hz), 4.06 (2H, t., J=6.0 Hz), 4.55 (2H, s.), 6.5-7.4 (4H, m.).

EXAMPLE 10

150 mg of N-[3-[3-(1-piperidinylmethyl)phenoxy]propyl]hydroxyacetamide was dissolved in 0.5 ml of pyridine, and 150 mg of benzoyl chloride was added dropwise to the solution under ice cooling. After the addition, the mixture was stirred at room temperature for 2 hours. The solvent was distilled off and water was added. The mixture was alkalized with aqueous ammonia, and extracted with ethyl acetate. The extract was dried over anhydrous magnesium sulfate, and the solvent was distilled off. The residue was separated and purified by TLC (developing solvent: chloroform/methanol=19/1) to afford 165 mg of N-[3-[3-(1-piperidinylmethyl)phenoxy]propyl]benzoyloxyacetamide.

IR(film, cm$^{-1}$): 1735, 1675. NMR(CDCl$_3$, δ): 1.3-2.7 (12H, m.), 3.43 (2H, s.), 3.50 (2H. q., J=6.5 Hz), 4.00 (2H, t., J=6.5 Hz), 4.75 (2H, s.), 6.5-8.2 (9H, m.).

The following compounds were obtained by repeating the above reaction using suitable amides and acid chlorides.

(i) N-[3-(3-Dimethylaminomethylphenoxy)propyl]benzoyloxyacetamide m.p: 46°-47° C. IR(KBr, cm$^{-1}$): 3300, 1728, 1660. NMR(CDCl$_3$, δ): 2.00 (2H, m., J=6.5 Hz), 2.20 (6H, s.), 3.32 (2H, s.), 3.52 (2H., q., J=6.5 Hz), 4.02 (2H, t., J=6.5 Hz), 4.76 (2H, s.), 6.5-8.1 (9H, m.).

(ii) N-(3,4-Dichlorobenzoyloxyacetyl)-3-(3-dimethylaminomethylphenoxy)propylamine m.p.: 48°-50° C. IR(KBr, cm$^{-1}$): 3300, 1730, 1660. NMR(CDCl$_3$, δ): 2.00 (2H, m., J=6.5 Hz), 2.21 (6H, s.), 3.32 (2H, s.), 3.56 (2H., q., J=6.5 Hz), 4.03 (2H, t., J=6.5 Hz), 4.77 (2H, s.), 6.5-8.1 (7H, m.).

(iii) N-(3,4-Dichlorobenzoyloxyacetyl)-3-[3-[1-(1-pyrrolidinyl)ethyl]phenoxy]propylamine IR(film, cm$^{-1}$): 3300, 1730, 1660. NMR(CDCl$_3$, δ): 1.33 (3H, d., J=7 Hz), 1.6-2.0 (4H, m.), 2.2-2.7 (4H, m.), 3.09 (1H, q., J=7 Hz), 3.54 (2H, q., J=6.5 Hz), 4.05 (2H, t., J=6.5 Hz), 4.79 (2H, s.), 6.5-8.2 (7H, m.).

(iv) N-3,4-Dichlorobenzoyloxyacetyl)-3-[3-(1-perhydroazepinylmethyl)phenoxy]propylamine m.p.: 75°-77° C. IR(KBr, cm$^{-1}$): 3280, 1740, 1660. NMR(CDCl$_3$, δ): 1.4-2.3 (12H, m.), 2.4-2.8 (4H, m.), 3.53 (2H, s.), 3.56 (2H, q., J=6.5 Hz), 4.05 (2H, t., J=6.5 Hz), 4.79 (2H, s.), 6.5-8.1 (7H, m.).

N-[3-[3-(1-Piperidinylmethyl)phenoxy]propyl]-pivaloyloxyacetamide

IR(film, cm$^{-1}$): 1735, 1665. NMR(CDCl$_3$, δ): 1.21 (9H, s.), 1.4-2.5 (12H, m.), 3.41 (2H, s.), 3.50 (2H, q., J=6.0 Hz), 4.01 (2H, t., J=6.0 Hz), 4.52 (2H, s.), 6.6-7.4 (4H, m.).

EXAMPLE 11

A solution of 645 mg of N-[3-[3-(1-piperidinylmethyl)phenoxy]propyl]hydroxyacetamide in 2 ml of N,N-dimethylformamide was added under ice cooling to a suspension of 84.3 mg of sodium hydride in 1 ml of N,N-dimethylformamide, and the mixture was stirred for 5 minutes. Then, a solution of 299.3 mg of methyl iodide in 1 ml of N,N-dimethylformamide was added dropwise under ice cooling, and the mixture was stirred for 10 minutes. After the stirring, water was added, and the mixture was extracted with ethyl acetate. The extract was dried over anhydrous magnesium sulfate, and the solvent was distilled off. The residue was separated and purified by TLC (developing solvent: chloroform/methanol=19/1) to afford 250 mg of N-[3-[3-(1-piperidinylmethyl)phenoxy]propyl]methoxyacetamide.

Melting point: 113°-115° C. (HCl salt). IR(film, cm$^{-1}$): 1670. NMR(CDCl$_3$, δ): 1.3-2.5 (12H, m.), 3.41 (3H, s.), 3.43 (2H, s.), 3.51 (2H, q., J=6.5 Hz), 3.89 (2H, s.), 4.05 (2H, t., J=6.5. Hz), 6.6-7.4 (4H, m.).

The following compound was obtained by repeating the above reaction using a suitable alkylating agent.

(i) N-[3-[3-[1-(1-Pyrrolidinyl)ethyl]phenoxy]propyl]ethoxyacetamide

IR(film, cm$^{-1}$): 1675. NMR(CDCl$_3$, δ): 1.22 (3H, t., J=6.5 Hz), 1.40 (3H, d., J=6.5 Hz), 1.6-2.8 (10H, m.), 3.19 (1H, q., J=6.5 Hz), 3.51 (2H, q., J=6.5 Hz), 3.56 (2H, q., J=6.5 Hz), 3.92 (2H, s.), 4.05 (2H, t., J=6.5 Hz), 6.6-7.4 (4H, m.).

EXAMPLE 12

300 mg of N-[3-[3-[1-(3-hydroxy)piperidinylmethyl]phenoxy]propyl]hydroxyacetamide was dissolved in 1 ml of chloroform, and 95 mg of acetic anhydride was added. The mixture was stirred at room temperature for 2 hours. Water and potassium carbonate was added to the reaction mixture and the mixture was extracted with chloroform. After drying, the solvent was distilled off. The residue was purified by TLC (developing solvent: chloroform/methanol=9/1) to afford 170 mg of N-[3-[3-[1-(3-hydroxy)piperidinylmethyl]phenoxy]propyl]acetoxyacetamide.

IR(film, cm$^{-1}$): 3320, 1750, 1665. NMR(CDCl$_3$, δ): 1.4-2.7 (8H, m.), 2.12 (3H, s.), 3.45 (2H, s.), 3.4-3.7 (5H, m.), 4.01 (2H, t., J=6 Hz), 4.50 (2H, s.), 6.7-7.3 (4H, m.).

EXAMPLE 13

(A) 3-[3-[1-(1-Pyrrolidinyl)ethyl]phenoxy]propylamine and bromopropionic acid were reacted in the same way as in Example 6 to afford N-[3-[3-[1-(1-pyrrolidinyl)ethyl]phenoxy]propyl]bromopropionamide.

IR(film, cm$^{-1}$): 1650. NMR(CD$_3$OD, δ): 1.76 (3H, d., J=6 Hz), 1.8-2.4 (6H, m.), 2.78 (2H, t., J=6 Hz), 3.0-3.8 (8H, m.), 4.08 (2H, t., J=6 Hz), 4.35 (1H, q., J=6 Hz), 6.8-7.5 (4H, m.).

(B) 500 mg of the amide compound obtained in step (A) was heated under reflux for 2 hours in 1 ml of ethanolamine and 1 ml of ethanol. The solvent was distilled off under reduced pressure, and potassium carbonate was added. The mixture was extracted with chloroform. The solvent was distilled off, and the residue was purified by TLC (developing solvent: chloroform/diethylamine=10:1) to afford 355 mg of N-[3-(2-hydroxyethylamino)propionyl]-3-[3-[1-(1-pyrrolidinyl)ethyl]-phenoxy]propylamine.

IR(KBr, cm$^{-1}$): 3300, 1650. NMR(CDCl$_3$, δ): 1.38 (3H, d., J=6 Hz), 1.6-2.2 (6H, m.), 2.2-2.9 (10H, m.), 3.0-3.8 (5H, m.), 4.01 (2H, t., J=6 Hz), 6.6-7.4 (4H, m.).

The following compounds were obtained by performing the reactions in steps (A) and (B) using suitable amines.

(i) N-[3-(2-Hydroxyethylamino)propionyl]-3-[3-(1-piperidinylmethyl)phenoxy]propylamine IR(film, cm$^{-1}$): 3420, 3280, 1650. NMR(CDCL$_3$, δ): 1.3-1.7 (6H, m.), 2.04 (2H, q., J=6 Hz), 2.3-2.6 (6H, m.), 2.6-3.4 (8H, m.), 3.43 (2H, s.), 3.55 (2H, q., J=6 Hz), 4.04 (2H, t., J=6 Hz), 6.7-7.3 (4H, m.).

(ii) N-[3-(2-Hydroxyethylamino)propionyl]-3-[3-(1-perhydroazocinylmethyl)phenoxy]propylamine IR(KBr, cm$^{-1}$): 3320, 1650. NMR(CDCl$_3$, δ): 1.3-1.8 (8H, m.), 1.98 (2H, m.), 2.2-3.1 (10H, m.), 3.2-3.8 (4H, m.), 3.57 (2H, s.), 4.00 (2H, t., J=6 Hz), 6.6-7.4 (4H, m.).

(iii) N-[3-(2-Hydroxyethylamino)propionyl]-3-[3-[1-(3-hydroxy)piperidinylmethyl]phenoxy]propylamine IR(film, cm$^{-1}$): 3300, 1650. NMR(CDCl$_3$, δ): 1.4-3.0 (14H, m.), 3.2-3.7 (7H, m.), 3.44 (2H, s.), 4.00 (2H, t., J=6 Hz), 6.7-7.3 (4H, m.).

(iv) N-[3-(2-Hydroxyethylamino)propionyl]-3-[3-[1-(4-hydroxy)piperidinylmethyl]phenoxy]propylamine IR(film, cm$^{-1}$): 3280, 1645. NMR(CDCl$_3$, δ): 1.6-3.0 (14H, m.), 3.3-3.7 (7H, m.), 3.43 (2H, s.), 4.02 (2H, t., J=6 Hz), 6.7-7.2 (4H, m.).

(v) N-[3-(2-Hydroxyethylamino)propionyl]-3-[3-[1-(3-hydroxymethyl)piperidinylmethyl]phenoxy]-propylamine IR(film, cm$^{-1}$): 3420, 3300, 1650. NMR(CDCl$_3$, δ): 1.5-3.0 (15H, m.), 3.2-3.7 (8H, m.), 3.43 (2H, s.), 4.00 (2H, t., J=6 Hz), 6.6-7.3 (4H, m.).

(vi) N-[3-(3-Hydroxypropylamino)propionyl]-3-[3-[1-(1-pyrrolidinyl)ethyl]phenoxy]propylamine NMR(CDCl$_3$, δ): 1.37 (3H, d., J=6.5 Hz), 1.5-2.2 (8H, m.), 2.3-3.0 (10H, m.), 3.0-3.8 (5H, m.), 4.01 (2H, t., J=6 Hz), 6.6-7.4 (4H, m.).

(vii) N-(3-Methylaminopropionyl)-3-[3-[1-(1-pyrrolidinyl)ethyl]phenoxy]propylamine IR(KBr, cm$^{-1}$): 3280, 1650. NMR(CD$_3$OD, δ): 1.38 (3H, d., J=7 Hz), 1.6-2.2 (6H, m.), 2.40 (3H, s.), 2.3-3.1 (8H, m.), 3.1-3.6 (3H, m.), 4.00 (2H, t., J=6 Hz), 6.6-7.4 (4H, m.).

(viii) N-(3-ethylaminopropionyl)-3-[3-[1-(1-pyrrolidinyl)ethyl]phenoxy]propylamine IR(KBr, cm$^{-1}$): 3280, 1650. NMR(CD$_3$OD, δ): 1.07 (3H, t., J=7 Hz), 1.36 (3H, d., J=6.5 Hz), 1.5-2.2 (6H, m.), 2.2-3.0 (10H, m.), 3.0-3.5 (3H, m.), 4.00 (2H, t., J=6.5 Hz), 6.6-7.4 (4H, m.).

(ix) N-(3-Dimethylaminopropionyl)-3-[3-[1-(1-pyrrolidinyl)ethyl]phenoxy]propylamine hydrobromide IR(film, cm$^{-1}$): 3280, 1650. NMR(CDCl$_3$, δ): 1.55 (3H, d., J=6 Hz), 1.7-2.2 (6H, m.), 2.23 (6H, s.), 2.3-3.1 (8H, m.), 3.43 (3H, q., J=6 Hz), 4.03 (2H, t., J=6 Hz), 6.6-7.4 (4H, m.).

EXAMPLE 14

43 mg of 50% sodium hydride was suspended in 0.5 ml of dry dimethylsulfoxide, and with stirring under ice cooling, a solution of 200 mg of 3-[3-[1-(1-pyrrolidinyl)ethyl]phenoxy]propylamine in 0.5 ml of dimethylsulfoxide was added dropwise. The mixture was stirred at room temperature for 20 minutes. Then, 105 mg of methyl α-hydroxyisobutyrate was added dropwise, and the mixture was stirred at room temperature for 1 hour. Ice water was added to the reaction mixture, and the mixture was extracted with chloroform. The organic layer was washed with water, and dried over anhydrous sodium sulfate. The solvent was distilled off, and the resulting crude oil was separated and purified by TLC (developing solvent: chloroform/methanol=9/1) to afford 71 mg of N-(2-hydroxy-2-methylpropionyl)-3-[3-[1-(1-pyrrolidinyl)ethyl]phenoxy]propylamine as an oil.

IR(film, cm$^{-1}$): 3400, 3360, 1650. NMR(CDCl$_3$, δ): 1.39 (3H, d., J=6 Hz), 1.42 (6H, s.), 1.55-2.15 (4H, m.), 2.25-2.75 (4H, m.), 3.00-3.66 (4H, m.), 4.04 (2H, t., J=6 Hz), 6.60-7.40 (4H, m.).

EXAMPLE 15

191 mg of 3-(1-piperidinylmethyl)phenol was dissolved in 10 ml of ethanol, and 116 mg of potassium hydroxide was added. The mixture was heated under reflux, and a solution of 360 mg of 3-acetamino-1-bromopropane in 3 ml of ethanol. The reaction mixture was heated under reflux for 8 hours, and the solvent was distilled off under reduced pressure. Water was added, and the mixture was extracted with chloroform. The organic layer was dried over anhydrous magnesium sulfate, and the solvent was distilled off under reduced pressure. The residue was purified by TLC (developing solvent: chloroform/methanol=9/1) to afford 205 mg of N-[3-[3-(1-piperidinylmethyl)phenoxy]propyl]acetamide as an oil. The resulting product coincided with the product obtained in Example 2.

EXAMPLE 16

236 mg of N-[3-[3-(1-aminoethyl)phenoxy]propyl]acetamide and 202 mg of triethylamine were dissolved in 10 ml of tetrahydrofuran, and a solution of 143 mg of 1,4-dichlorobutan-2-ol in 5 ml of tetrahydrofuran was added dropwise with stirring. The mixture was stirred at room temperature for 1 hour, and poured into a dilute aqueous solution of potassium carbonate. The organic layer was extracted with chloroform. The chloroform layer was dried, and the solvent was distilled off. The residue was purified by TLC (developing solvent: chloroform/methanol=9/1) to afford 168 mg of N-[3-[3-[1[1-(3-hydroxy)pyrrolidinyl]ethyl]phenoxy]propyl]acetamide as an oil.

This product coincided with the product obtained in Example 3, (i).

PRODUCTION EXAMPLE 1

Piperidine (26 g) and 4.7 g of sodium borohydride were added to a solution of 15 g of 3-hydroxybenzaldehyde in 100 ml of ethanol, and the mixture was stirred until a complete solution formed. The solution was allowed to stand overnight at room temperature. Under reduced pressure, the solvent was distilled off, and 200 ml of ice water was added to the residue. The mixture was acidified with hydrochloric acid, and allowed to stand for 1 hour. The raw material was extracted away using ethyl acetate, and the aqueous solution was separated. The aqueous layer was alkalized with aqueous ammonia, and the precipitated oily product was extracted with ethyl acetate. The solvent was distilled off, and the residue was recrystallized from acetone/n-hexane to afford 17.5 g of 3-(1-piperidinylmethyl)phenol.

Melting point: 135.8°-138.0° C. NMR(CDCl$_3$, δ): 1.30-1.85 (6H, m.), 2.20-2.60 (4H, m.), 3.42 (2H, s.), 6.60-7.20 (4H, m.), 7.43 (1H, s.).

The following compounds were produced by repeating the above reaction using suitable carbonyl compounds and amines.

(i) 3-[1-(1-Pyrrolidinyl)ethyl]phenol b.p.: 166°-176° C./6mmHg. IR(film, cm$^{-1}$): 1603, 1590. NMR(CDCl$_3$, δ): 1.39 (3H, d., J=6 Hz), 1.55-1.95 (4H, m.), 2.2-2.9 (4H, m.), 3.19 (1H, q., J=6 Hz), 6.6-7.3 (4H, m.), 8.44 (1H, s.).

(ii) 3-[1-(1-Piperidinyl)ethyl]phenol m.p.: 135.6°-140.0° C.

IR(KBr, cm$^{-1}$): 1613, 1585. NMR(CD$_3$OD, δ): 1.35 (3H, d., J=6 Hz), 1.20-1.30 (6H, m), 2.20-2.15 (4H, m.), 3.32 (1H, q., J=6 Hz), 6.5-7.2 (4H, m.).

(iii) 3-[1-(1-Perhydroazepinyl)ethyl]phenol
NMR(CDCl$_3$, δ): 1.35 (3H, d., J=7 Hz), 1.57 (8H, m.), 2.70 (4H, m.), 3.69 (1H, q., J=7 Hz), 6.5-7.4 (4H, m.).

(iv) 3-[1-(1-Pyrrolidinyl)propyl]phenyl
NMR(CDCl$_3$, δ): 0.64 (3H, t., J=7 Hz), 1.4-2.1 (6H, m.), 2.1-2.8 (4H, m.), 2.95 (1H, q., J=5 Hz), 6.6-7.3 (4H, m.), 8.02 (1H, s.).

PRODUCTION EXAMPLE 2

2.74 g of 3-hydroxy-α-methylbenzylamine, 2.9 g of 1,4-dichlorobutan-2-ol, 3.4 g of anhydrous potassium carbonate and 80 ml of dry ethanol were heated under reflux for 24 hours. The reaction mixture was cooled, and the precipitated salt was removed by filtration. The solvent was distilled off. The residue was separated and purified by TLC (developing solvent: chloroform/methanol=9/1) to afford 2.2 g of 3-[1-[1-(3-hydroxy)pyrrolidinyl]ethyl]phenol as an oil.

IR(film, cm$^{-1}$): 3300. NMR(CDCl$_3$, δ): 1.32 (3H, d., J=6 Hz), 1.7-3.4 (7H, m.), 4.3 (1H, m.), 5.7 (2H, s.), 6.6-7.2 (4H, m.).

PRODUCTION EXAMPLE 3

15 g of 3-(1-piperidinylmethyl)phenol was dissolved in 80 ml of dry dimethylformamide. The solution was gradually added dropwise to a suspension of 3.14 g of 60% sodium hydride in 30 ml of dry dimethylformamide with stirring under ice cooling. After the addition, the mixture was stirred at room temperature for 20 minutes, and 21 g of N-bromopropylphthalimide was added. The mixture was reacted at room temperature for 1 hour, and ice water was added. The mixture was extracted with chloroform, washed with water and dried over anhydrous magnesium sulfate. Distilling off the solvent afforded 28.5 g of N-[3-[3-(1-piperidinylmethyl)phenoxy]propyl]phthalamide as an oil.

IR(film, cm$^{-1}$): 1778, 1720. NMR(CDCl$_3$, δ): 1.35-1.70 (6H, m.), 2.21 (2H, q., J=6 Hz), 3.47 (2H, s.), 3.88 (2H, t., J=6 Hz), 3.99 (2H, t., J=6 Hz), 6.60-7.10 (4H, m.), 7.60-7.90 (4H, m.).

The following compounds were produced by repeating the above reaction using suitable phenols.

(i) N-[3-[3-[1-(1-Pyrrolidinyl)ethyl]phenoxy]-propyl]phthalimide b.p.: 240°–243° C./0.5 mmHg. IR(film, cm$^{-1}$): 1780, 1720, 1603, 1590. NMR(CDCl$_3$, δ): 1.35 (3H, d., J=6 Hz), 1.55–1.95 (4H, m.), 2.0–2.7 (6H, m.), 3.10 (1H, q., J=6 Hz), 3.87 (2H, t., J=6 Hz), 4.00 (2H, t., J=6 Hz), 6.52–7.25 (4H, m.), 7.55–7.94 (4H, m.).

(ii) N-[3-[3-[1-(1-Piperidinyl)ethyl]phenoxy]-propyl]phthalimide

IR(film, cm$^{-1}$): 1772, 1710. NMR(CDCl$_3$, δ): 1.30 (3H, d., J=7 Hz), 1.25–1.75 (6H, m.), 2.22 (2H, q., J=6 Hz), 2.25–2.50 (4H, m.), 3.32 (1H, q., J=7 Hz), 3.90 (2H, t., J=6 Hz), 4.02 (2H, t., J=6 Hz), 6.60–7.90 (8H, m.).

(iii) N-[3-[3-[1-(1-Perhydroazepinyl)ethyl]phenoxy]-propyl]phthalimide

NMR(CDCl$_3$, δ): 1.29 (3H, d., J=7 Hz), 1.57 (8H, m.), 2.18 (2H, m., J=7 Hz), 2.60 (4H, m.), 3.68 (1H, q., J=7 Hz), 3.90 (2H, t., J=7 Hz), 4.02 (2H, t., J=7 Hz), 6.5–8.0 (8H, m.).

(iv) N-[3-[3-[1-(1-Perhydroazocinyl)ethyl]phenoxy]-propyl]phthalimide

NMR(CDCl$_3$, δ): 1.28 (3H, d., J=7 Hz), 1.57 (10H, m.), 2.17 (2H, m., J=7 Hz), 2.5 (4H, m.), 3.60 (1H, q., J=7 Hz), 3.90 (2H, t., J=7 Hz), 4.02 (2H, t., J=7 Hz), 6.5–8.0 (8H, m.).

(v) N-[3-[3-[1-(1-Pyrrolidinyl)propyl]phenoxy]-propyl]phthalimide

IR(film, cm$^{-1}$): 1780, 1720. NMR(CDCl$_3$, δ): 0.64 (3H, t., J=7 Hz), 1.5–2.7 (12H, m.), 2.90 (1H, q., J=5 Hz), 3.90 (2H, t., J=7 Hz), 4.03 (2H, t., J=6 Hz), 6.5–7.3 (4H, m.), 7.5–8.0 (4H, m.).

(vi) N-[3-[3-[1-[1-(3-Hydroxy)pyrrolidinyl]ethyl]-phenoxy]propyl]phthalimide

IR(film, cm$^{-1}$): 3480, 1775, 1710.

PRODUCTION EXAMPLE 4

(A) A solution of 2.6 g of 3-hydroxybenzyl alcohol in 10 ml of dry dimethylsulfoxide was added dropwise with stirring under ice cooling to a suspension of 0.88 g of 60% sodium hydride in 5 ml of dry dimethylsulfoxide. After the addition, the mixture was stirred at room temperature for 20 minutes, and 6 g of N-bromopropylphthalimide was added. The mixture was reacted at room temperature for 1 hour, and ice water was added. The mixture was extracted with ether, washed with water, and dried over anhydrous sodium sulfate. The solvent was distilled off, and the residue was crystallized with ether to afford 2.6 g of N-[3-[3-(hydroxymethyl)phenoxy]propyl]phthalimide.

Melting point: 82.0°–83.5° C. IR(KBr, cm$^{-1}$): 3510, 1773, 1705. NMR(CDCl$_3$, δ): 2.15 (2H, m., J=7 Hz), 3.88 (2H, t., J=7 Hz), 4.00 (2H, s.), 4.5–4.7 (3H, m.), 6.6–7.3 (4H, m.), 7.5–7.9 (4H, m.).

(B) 2.5 g of N-[3-[3-(hydroxymethyl)phenoxy]-propyl]phthalimide was dissolved in 12 ml of benzene, and 3 ml of thionyl chloride was added. The mixture was refluxed for 1 hour. The solvent was distilled off under reduced pressure, and the residue was dissolved in ether. The solution was washed twice with a 5% aqueous solution of potassium carbonate, and then rinsed with water. The product was dried over anhydrous sodium sulfate, and the solvent was distilled off to afford 2.8 g of N-[3-[3-(chloromethyl)phenoxy]propyl]phthalimide as an oil.

NMR(CDCl$_3$, δ): 2.17 (2H, m., J=7 Hz), 3.79 (2H, t., J=7 Hz), 4.01 (2H, t., J=7 Hz), 4.49 (2H, s.), 6.6–7.3 (4H, m.), 7.5–7.9 (4H, m.).

(C) 1.0 g of N-[3-[3-(chloromethyl)phenoxy]-propyl]phthalimide and a solution of 0.5 g of 3-hydroxypyrrolidine in 5 ml of dry tetrahydrofuran were refluxed for 2 hours. The product was cooled, and the precipitated salt was removed by filtration. The solvent was distilled off. The residue was separated and purified by TLC (developing solvent: chloroform/methanol=9/1) to afford 315 mg of N-[3-[3-[1-(3-hydroxy)pyrrolidinylmethyl]phenoxy]propyl]phthalimide as an oil.

IR(film, cm$^{-1}$): 3420, 1770, 1710. NMR(CDCl$_3$, δ): 1.7–2.9 (8H, m.), 3.52 (2H, s.), 3.85 (2H, t., J=6 Hz), 4.00 (2H, t., J=6 Hz), 4.3 (1H, m.), 6.6–7.3 (4H, m.), 7.5–7.9 (4H, m.).

The following compounds were produced in the same way as in step (C) using suitable amines.

(i) N-[3-[3-(1-Perhydroazepinylmethyl)phenoxy]-propyl]phthalimide

IR(film, cm$^{-1}$): 1780, 1720. NMR(CDCl$_3$, δ): 1.4–1.9 (8H, m.), 1.9–2.4 (2H, m.), 2.4–2.8 (4H, m.), 3.56 (2H, s.), 3.89 (2H, t., J=6 Hz), 6.5–7.3 (4H, m.), 7.5–8.0 (4H, m.).

(ii) N-[3-[3-[1-(3-Hydroxy)piperidinylmethyl]phenoxy]propyl]phthalimide

NMR(CDCl$_3$, δ): 1.6 (4H, m.), 2.0–2.6 (6H, m.), 3.44 (1H, broad s.), 3.48 (2H, s.), 3.8 (1H, m.), 3.90 (2H, t., J=7 Hz), 4.02 (2H, t., J=7 Hz), 6.6–7.3 (4H, m.), 7.6–7.9 (4H, m.).

(iii) N-[3-[3-[1-(4-Hydroxy)piperidinylmethyl]-phenoxy]propyl]phthalimide

NMR(CDCl$_3$, δ): 1.6–2.4 (9H, m.), 2.6–2.9 (2H, m.), 3.4 (1H, m.), 3.49 (2H, s.), 3.91 (2H, t., J=7 Hz), 4.02 (2H, t., J=7 Hz), 6.6–7.3 (4H, m.), 7.6–7.9 (4H, m.).

PRODUCTION EXAMPLE 5

28 g of N-[3-[3-(1-piperidinylmethyl)phenoxy]-propyl]phthalimide was dissolved in 200 ml of ethanol, and 46.2 ml of hydrazine hydrate was added. The mixture was allowed to stand at room temperature for 1 hour. The solvent was distilled off under reduced pressure. Benzene (200 ml) was added, followed by azeotropic distillation. Chloroform (100 ml) was added to the residue, and the insoluble matter was removed by filtration.

The solvent was distilled off, and the residue was distilled under reduced pressure to afford 13.7 g of 3-[3-(1-piperidinylmethyl)phenoxy]propylamine.

Boiling point: 155°–158° C./0.25 mmHg. IR(film, cm$^{-1}$): 3360, 3295. NMR(CDCl$_3$, δ): 1.30–1.70 (6H, m.), 1.95 (2H, q., J=6 Hz), 2.23–2.62 (6H, m.), 2.90 (2H, t., J=6 Hz), 3.42 (2H, s), 3.99 (2H, t., J=6 Hz), 6.60–7.30 (4H, m.).

The following Compounds were produced by repeating the above reaction using suitable phthalimide compounds.

(i) 3-[3-[1-(1-Pyrrolidinyl)ethyl]phenoxy]propylamine b.p.: 170°–176° C./2 mmHg. IR(film, cm$^{-1}$): 3400, 1603, 1590. NMR(CDCl$_3$, δ): 1.36 (3H, d., J=6 Hz), 1.55–2.15 (8H, m.), 2.2–2.7 (4H, m.), 2.90 (2H, t., J=6 Hz), 3.14 (1H, q., J=6 Hz), 4.02 (2H, t., J=6 Hz), 6.60–7.34 (4H, m.).

(ii) 3-[3-[1-(1-Piperidinyl)ethyl]phenoxy]propylamine

IR(film, cm$^{-1}$): 3340, 3290, 1600, 1594. NMR(CDCl$_3$, δ): 1.41 (3H, d., J=7 Hz), 1.35–1.70 (8H, m.), 1.94 (2H, q., J=6 Hz), 2.21–2.55 (4H, m.), 2.91 (2H, t., J=6 Hz), 3.32 (1H, q., J=7 Hz), 4.02 (2H, t., J=6 Hz), 6.65–7.30 (4H, m.).

(iii) 3-[3-[1-(1-Pyrrolidinyl)propyl]phenoxy]propylamine

IR(film, cm$^{-1}$): 3360, 3280. NMR(CDCl$_3$, δ): 0.66 (3H, t., J=8 Hz), 1.4–2.1 (8H, m.), 2.2–2.7 (4H, m.), 2.7–3.1 (3H, m.), 4.02 (2H, t., J=6 Hz), 6.6–7.4 (4H, m.).

(iv) 3-[3-[1-(3-Hydroxy)pyrrolidinylmethyl]phenoxy]propylamine

IR(film, cm$^{-1}$): 3320, 1600, 1580.

(v) 3-[3-(1-Perhydroazepinylmethyl)phenoxy]propylamine

IR(film, cm$^{-1}$): 3360, 3280. NMR(CDCl$_3$, δ): 1.4–2.2 (10H, m.), 2.4–2.8 (4H, m.), 2.90 (2H, t., J=7 Hz), 3.58 (2H, s.), 4.02 (2H, t., J=6 Hz), 6.6–7.4 (4H, m.).

(vi) 3-[3-[1-(3-Hydroxy)piperidinylmethyl]phenoxy]propylamine

IR(film, cm$^{-1}$): 3360, 1603, 1585. NMR(CDCl$_3$, δ): 1.6 (4H, m.), 1.7–2.6 (9H, m.), 2.88 (2H, t., J=6 Hz), 3.45 (2H, s.), 3.7 (1H, m.), 4.00 (2H, t., J=6 Hz), 6.7–7.3 (4H, m.).

(vii) 3-[3-[1-(4-Hydroxy)piperidinylmethyl]phenoxy]propylamine

IR(film, cm$^{-1}$): 3360, 1605, 1590. NMR(CDCl$_3$, δ): 1.6–2.5 (11H, m.), 2.6–2.9 (2H, m.), 2.09 (2H, t., J=6 Hz), 3.44 (2H, s.), 3.6 (1H, m.), 4.01 (2H, t., J=6 Hz), 6.7–7.5 (4H, m.).

(viii) 3-[3-[1-[1-(3-Hydroxy)pyrrolidinyl]ethyl]phenoxy]propylamine

IR(film, cm$^{-1}$): 3360, 1600, 1592. NMR(CDCl$_3$, δ): 1.35 (3H, d., J=7 Hz), 1.7–3.3 (14H, m.), 4.02 (2H, t., J=6 Hz), 4.3 (1H, m.), 6.6–7.3 (4H, m.).

Examples of the production of pharmaceutical preparations containing the compound of the present invention are given below.

EXAMPLE A

Tablets:

Tablets each containing 50 mg or 100 mg of the active compound are prepared as follows:

| Prescription 1-a (50 mg tablet) | |
|---|---|
| | mg/tablet |
| N-[3-[3-(1-Piperidinylmethyl)phenoxy]propyl]acetoxyacetamide hydrochloride | 50 |
| Lactose | 92.2 |
| Starch | 44.8 |
| Calcium carboxymethyl cellulose | 10 |
| Talc | 2 |
| Magnesium stearate | 1 |
| | 200.0 mg |

| Prescription 1-b (100 mg tablet) | |
|---|---|
| | mg/tablet |
| N-[3-[3-(1-Piperidinylmethyl)phenoxy]propyl]acetoxyacetamide hydrochloride | 100 |
| Lactose | 42.2 |
| Starch | 44.8 |
| Calcium carboxymethyl cellulose | 10 |
| Talc | 2 |
| Magnesium stearate | 1 |
| | 200.0 mg |

Crystals N-[3-[3-(1-piperidinylmethyl)phenoxy]propyl]acetoxyacetamide hydrochloride are pulverized to less than 70 microns, and lactose and starch are added, followed by thorough mixing. A 10% starch paste was added to the mixed powder, and they were mixed with stirring to prepare granules. After dry granulation, the particle size of the granules was maintained uniform at about 840 microns. Talc and magnesium stearate were mixed with the granules, and tablets were produced from the granules.

EXAMPLE B

Capsules:

| Prescription 2 (50 mg capsule) | |
|---|---|
| | mg/capsule |
| N-[3-[3-(1-Piperidinylmethyl)phenoxy]propyl]acetoxyacetamide hydrochloride | 50 |
| Starch | 30 |
| Lactose | 27.8 |
| Magnesium stearate | 2.2 |
| | 110.0 mg |

N-[3-[3-(1-Piperidinylmethyl)phenoxy]propyl]acetoxyacetamide hydrochloride was finely pulverized, and starch, lactose and magnesium stearate was added to the pulverized product. They were mixed well, and the mixture was filled into No. 5 capsules.

What we claim is:

1. A phenoxypropylamine derivative of the following formula

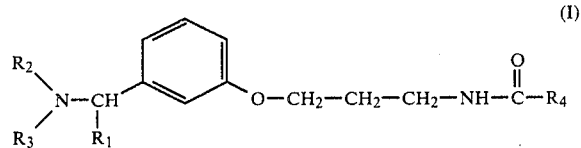

wherein R$_1$ represents a hydrogen atom or a methyl or ethyl group, R$_2$ and R$_3$, independently from each other, represent a lower alkyl group, or together form a linear alkylene group having 4 to 7 carbon atoms which may be optionally substituted by a hydroxyl or hydroxymethyl group, and R$_4$ represents a hydrogen atom or a group of the formula —R$_5$—Z in which R$_5$ represents a lower alkylene group, and Z represents a hydrogen atom or an amino, mono- or di-(lower alkyl)amino, hydroxy lower alkylamino, lower alkanoylamino, hydroxyl, lower alkoxy, lower alkanoyloxy, phenoxy, halophenoxy, benzoyloxy or halobenzoyloxy group, or a pharmaceutically acceptable salt thereof.

2. A compound according to claim 1 wherein the moiety

represents a 1-pyrrolidinyl or 1-piperidinyl group which may be optionally substituted by a hydroxyl group.

3. A compound according to claim 1 wherein R$_5$ represents a methylene or ethylene group.

4. A compound according to claim 1 wherein Z represents a hydrogen atom, an amino group, a mono- or dimethylamino group, a hydroxyethylamino group, an acetylamino group, a hyroxyl group, a C$_1$–C$_2$ alkoxy group or a C$_2$–C$_3$ alkanoyloxy group.

5. A compound according to claim 1 wherein the moiety

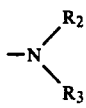

represents a 1-pyrrolidinyl or 1-piperidinyl group.

6. A compound according to claim 5 wherein $R_1$ represents a hydrogen atom or a methyl group.

7. A compound according to claim 1 wherein $R_4$ represents a hydrogen atom or a methyl, hydroxyethylaminoethyl, hydroxymethyl, methoxymethyl, ethoxymethyl, acetoxymethyl or propionyloxymethyl group.

8. A compound according to claim 1 wherein $R_4$ represents a hydroxymethyl or acetoxymethyl group.

9. A compound according to claim 1 which is N-[3-[3-[1-(1-pyrrolidinyl)ethyl]phenoxy]propyl]formamide, N-[3-[3-[1-(1-pyrrolidinyl)ethyl]phenoxy]propyl]acetamide, N-[3-[3-[1-(1-pyrrolidinyl)ethyl]phenoxy]propyl]hydroxyacetamide, N-[3-[3-(1-piperidinylmethyl)phenoxy]propyl]acetamide, N-[3-[3-(1-piperidinylmethyl)phenoxy]propyl]hydroxyacetamide, N-[3-[3-(1-piperidinylmethyl)phenoxy]propyl]acetoxyacetamide, N-[3-[3-(1-piperidinylmethyl)phenoxy]propyl]methoxyacetamide, N-[3-[3-(1-perhydroazepinylmethyl)phenoxy]propyl]hydroxyacetamide, N-[3-[3-[1-(3-hydroxy)piperidinylmethyl]phenoxy]propyl]formamide, or a pharmaceutically acceptable salt of any one of these compounds.

10. A compound according to claim 1 which is N-[3-[3-(1-piperidinylmethyl)phenoxy]propyl]acetoxyacetamide or a pharmaceutically acceptable salt thereof.

11. An antiulcer composition comprising an antiulcer effective amount of a compound according to any one of claims 1 to 10, or a pharmaceutically acceptable salt thereof, and a pharmaceutically acceptable carrier or diluent.

12. Method for the treatment of ulcers of the stomach or duodenum, which comprises administering to a patient suffering therefrom an antiulcer effective amount of a compound according to any one of claims 1 to 10 or a pharmaceutically acceptable salt thereof.

* * * * *